United States Patent [19]

Hamer et al.

[11] Patent Number: 5,187,165
[45] Date of Patent: Feb. 16, 1993

[54] MEMORY ENHANCING AND ANALGESIC 1,2,3,3A,8,8A-HEXAHYDRO-3A,8(AND 1,3A,8)-DI(AND TRI)METHYLPYRROLO[2,3-B]INDOLES

[75] Inventors: Russell R. L. Hamer, Far Hills; Grover C. Helsley, Pluckemin; Edward J. Glamkowski, Warren; Yulin Chiang, Convent Station; Brian S. Freed, Somerset; Barbara E. Kurys, Elmwood Park, all of N.J.

[73] Assignee: Hoechst-Roussel Pharmaceuticals Inc., Somerville, N.J.

[21] Appl. No.: 247,826

[22] Filed: Sep. 22, 1988

Related U.S. Application Data

[63] Continuation-in-part of Ser. No. 49,894, May 15, 1987, Pat. No. 4,791,107, which is a continuation-in-part of Ser. No. 885,991, Jul. 16, 1996, abandoned.

[51] Int. Cl.$^5$ ............... C07D 471/04; A61K 31/475
[52] U.S. Cl. .................................. 514/307; 546/147
[58] Field of Search ............... 540/480, 583, 602; 544/58.4, 58.5, 142, 158, 372; 546/146, 199, 271, 147; 548/316, 406, 407, 429; 514/212, 216, 228.2, 232.8, 253, 307, 322, 338, 392, 409, 411

[56] References Cited

U.S. PATENT DOCUMENTS

| | | | |
|---|---|---|---|
| 4,680,172 | 7/1987 | Leeson | 424/449 |
| 4,831,155 | 5/1989 | Brufani et al. | 548/429 |
| 4,900,748 | 2/1990 | Brossi et al. | 548/429 X |
| 4,978,673 | 12/1990 | Meroni et al. | 548/429 X |
| 4,983,616 | 1/1991 | O'Malley et al. | 548/429 X |

FOREIGN PATENT DOCUMENTS 0154864  9/1985  European Pat. Off. .

OTHER PUBLICATIONS

P. Julian et al. *J. Am. Chem. Soc.*, 57 563 (1935).
Yu and Brossi, *Heterocycles*, vol. 27, No. 3, pp. 745–750 (1988).
Chem. Abstracts, vol. 108 221937m (1988).
Cowin, "Silicon in Oganic Synthesis," Chapter 10, pp. 125–133 Butterworths, (1981).

*Primary Examiner*—Joseph Paul Brust
*Assistant Examiner*—Mary Susan H. Gabilan
*Attorney, Agent, or Firm*—Tatsuya Ikeda

[57] ABSTRACT

There are disclosed various derivatives of eseroline and related compounds of the formula below

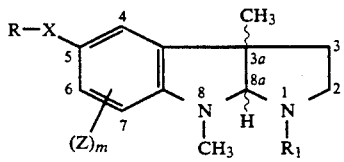

where $R, R_1, X, Z$ and m are as defined in the specification, which compounds being useful for enhancing cholinergic function, as antidepressant agents and as analgesic agents.

18 Claims, No Drawings

MEMORY ENHANCING AND ANALGESIC 1,2,3,3A,8,8A-HEXAHYDRO-3A,8(AND 1,3A,8)-DI(AND TRI)METHYLPYRROLO[2,3-B]INDOLES

This is a continuation-in-part application of a prior patent application Ser. No. 049,894, filed May 15, 1987 now U.S. Pat. No. 4,791,107, which is a continuation-in-part of a prior application Ser. No. 885,991, filed Jul. 16, 1986 now abandoned.

The present invention relates to compounds of the formula,

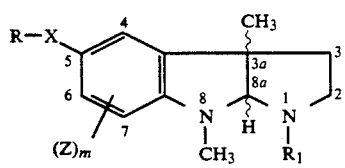

where
(a) X is O or S;
(b) R is H, loweralkyl,

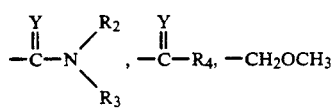

or triloweralkylsilyl;
where Y is O or S; $R_2$ is alkyl, cycloalkyl, spiroalkyl, bicycloalkyl, bicycloalkylmethyl, tricycloalkyl, tricycloalkylmethyl,

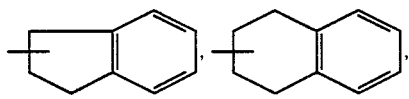

cycloalkenyl, aryl, arylloweralkyl, heteroaryl or heteroarylloweralkyl, $R_3$ is H or alkyl, or the group $-NR_2R_3$ taken as a whole is

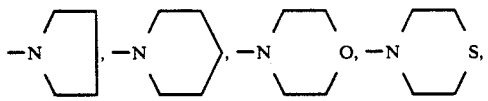

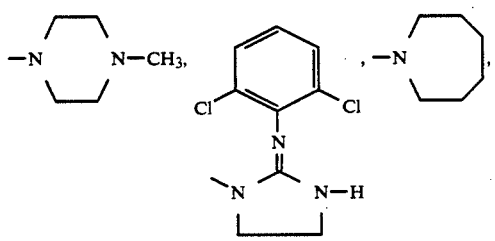

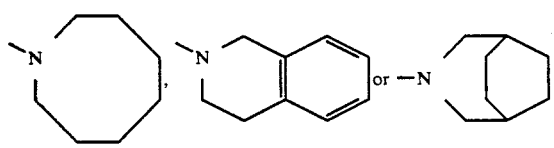

and $R_4$ is hydrogen, loweralkyl, arylloweralkyl, diarylloweralkyl, aryl or heteroaryl,
(c) m is 1 or 2;
(d) Each Z is independently H, loweralkyl, halogen, nitro, $-NH_2$, loweralkylcarbonylamino, arylcarbonylamino, loweralkoxycarbonylamino, loweralkylamino, triloweralkylsilyl, formyl, loweralkylaminocarbonyl, carboxyl or loweralkoxycarbonyl, and
(e) $R_1$ is H, loweralkyl, arylloweralkyl, heteroarylloweralkyl, cycloalkylmethyl or loweralkenylmethyl, with the proviso that when X is O, m is 1, Z is H and $R_1$ is methyl, R is not $-CONHCH_3$, $-CONHC_6H_5$, hydrogen, methyl or ethyl, and that when X is O, m is 1 and Z and $R_1$ are both hydrogen, R is not hydrogen or methyl, which are useful for enhancing cholinergic function, as antidepressant agents and as analgesic agents; pharmaceutical compositions comprising an effective amount of such a compound; a method of treating a patient in need of memory enhancement comprising the administration of such a compound of the patient and a method of relieving pain comprising the administration of such a compound to the patient.

Subgeneric to the compounds of formula I above are compounds of formula II below

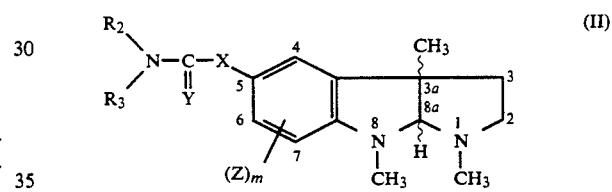

where X, Y, Z, $R_2$ and $R_3$ are as defined earlier with the proviso that when X and Y are both oxygen and Z and $R_3$ are both hydrogen, $R_2$ is not methyl or phenyl.

Also subgeneric to the compounds of formula I above are compounds of formula III below

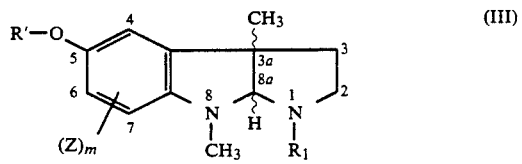

where $R_1$, Z and m are as defined earlier and R' is H, loweralkyl,

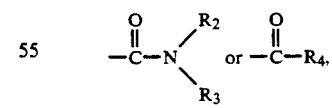

where $R_2$, $R_3$ and $R_4$ are as defined earlier with the proviso that when m is 1 and Z is hydrogen and $R_1$ is methyl, R' is not $-CONHCH_3$, $-CONHC_6H_5$, hydrogen, methyl or ethyl, and that when m is 1 and Z and $R_1$ are both hydrogen, R' is not hydrogen or methyl.

Unless otherwise stated or indicated, the following definitions shall apply throughout the specification and the appended claims.

The term alkyl shall mean a straight or branched alkyl group having from 1 to 22 carbon atoms. Examples of said alkyl include methyl, butyl, octyl, octadecyl etc.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term cycloalkyl shall mean a cycloalkyl group having from 3 to 18 carbon atoms in the ring. Said cycloalkyl group may be substituted with 1 or 2 loweralkyl groups.

The term spiroalkyl shall mean a spiroalkyl group having from 7 to 18 carbon atoms.

The term cycloalkenyl shall mean a cycloalkenyl group containing 3 to 18 carbon atoms in the ring and having only one double bond in the ring. Said cycloalkenyl group may be substituted with 1 or 2 loweralkyl groups.

The term bicycloalkyl shall mean a bicyloalkyl group having from 7 to 18 carbon atoms in the ring system.

The term bicycloalkylmethyl shall mean a methyl group which is substituted with a bicycloalkyl group.

The term tricycloalkyl shall mean a tricycloalkyl group having 10 to 18 carbon atoms in the ring system.

The term tricycloalkylmethyl shall mean a methyl group which is substituted with a tricycloalkyl group.

The term halogen shall mean fluorine, chlorine, bromine or iodine.

The term aryl shall mean an unsubstituted phenyl group or naphthyl group, or a phenyl group substituted with 1, 2 or 3 substituent groups each of which being independently loweralkyl, halogen, nitro, loweralkoxy, hydroxy, or trifluoromethyl.

The term heteroaryl shall mean a group having the formula

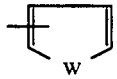

where W is O, S, $NR_5$ or CH=N, $R_5$ being hydrogen or loweralkyl and it shall include all the positional isomers. Thus, for instance, when W is S, the formula includes both 2-thienyl and 3-thienyl.

The compounds of this invention are prepared by utilizing one or more of the steps described below.

Throughout the description of the synthetic steps, the notations, X, R, $R_1$ through $R_5$, Y, Z and m shall have the respective meanings given above unless otherwise stated or indicated, and other notations shall have the respective meanings defined in their first appearances unless otherwise stated or indicated.

In structural formulas depicting the compounds of this invention, heavy lines (━━━) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines ( I I I I I ) signify that the two substituents are below the average plane of the three-ring system, and wavy lines (∼∼∼) signify that the two substituents are both either above or below said average plane. Because of conformational constraints, the two substituents at the 3a- and 8a-positions must be both above said average plane or both below said average plane. Thus, in formulas (I), (II) and (III), the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis. These two types of configuration are depicted below.

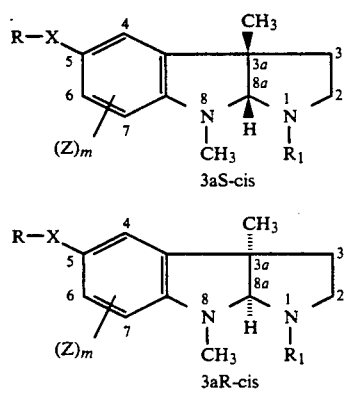

Throughout the specification and the appended claims, when the inventors intend to designate in a single formula (to save space) that the compound is 3aS-cis, or 3aR-cis, or a racemic or other mixture of the two, that formula will contain wavy lines, as depicted below

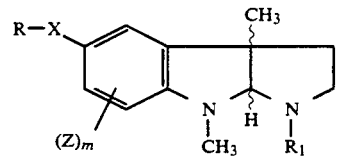

It is the intent of the present inventors to claim both of said cis isomers, namely, 3aS-cis isomer and 3aR-cis isomer for each compound name or structural formula although sometimes only one isomer is shown in the specification in order to save space. It is also the intent of the present inventors to claim all mixtures of the 3aS-cis and 3aR-cis isomers including the racemic mixture (1:1 ratio of 3aS-cis:3aR-cis).

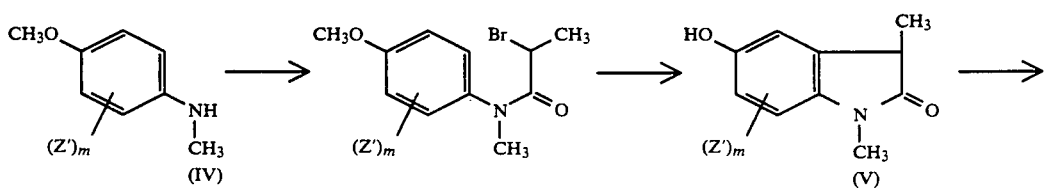

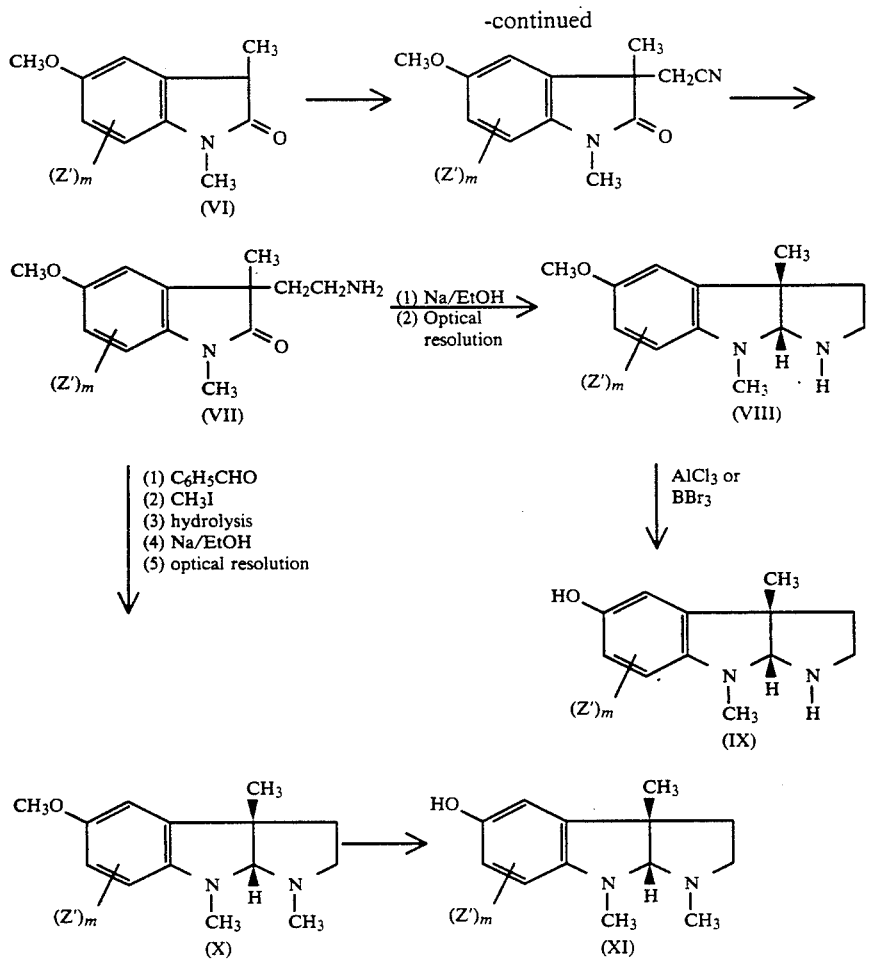

STEP A

Starting with a compound of formula IV (where Z' is hydrogen, loweralkyl, halogen or nitro) and utilizing the synthetic scheme disclosed in Julian et al., J. Chem. Soc., 1935, 563–566 and 755–757, one can prepare compounds of the formulas VIII through XI. The synthetic scheme is outlined below, but for details the reader is referred to the original articles. For details of another optical resolution procedure not described in Julian et al., the reader is referred to Schonenberger et al., J. Med. Chem., 1986, Volume 29, 2268–2273; and Schonenberger et al., Helv. Chim. Acta, 1986, Volume 69, 283–287 and 1486–1497.

If, in the synthetic scheme presented in the diagram depicted above, the conversion of compound VII to compound VIII is conducted without the optical resolution step, a racemic compound depicted by formula VIIIa is obtained. Said racemic compound is a 50:50 mixture of compound VIII and its 3aR-cis isomer, and it is used as a starting material for preparing other racemic compounds falling within the scope of this invention.

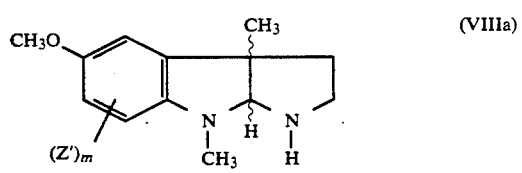

(VIIIa)

STEP B

As an alternative to STEP A above, one can introduce Cl, Br or $NO_2$ into the $C_7$-position of compound Xa and obtain compound Xb depicted below (where Z is Cl, Br or $NO_2$) by reacting compound Xa with N-chlorosuccinimide, N-bromosuccinimide or $NO_2BF_4$, respectively, according to a routine procedure known in the art.

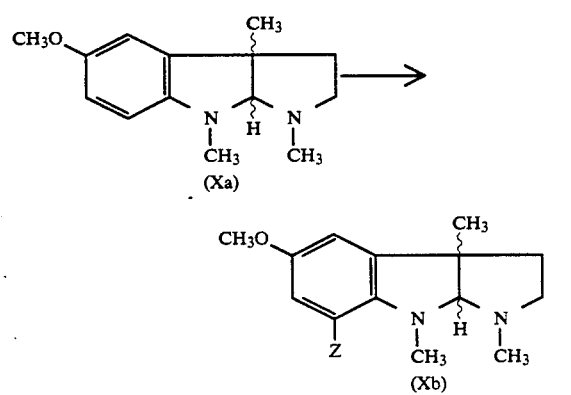

(Z = Cl, Br or $NO_2$)

STEP C

Compound XI can readily be converted to an ether compound of formula XII where R' is loweralkyl, methoxymethyl or triloweralkylsilyl according to a routine method known in the art. Thus, for instance, when R' is ethyl, compound XI is reacted with ethyl p-toluenesulfonate to obtain the ethyl ether, when R' is methoxymethyl, $CH_3OCH_2Br$ is used as a reactant, and when R' is tri-isopropylsilyl, $(i-Pr)_3SiCl$ is used as a reactant.

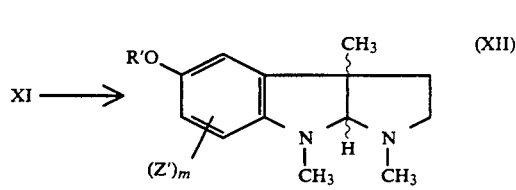

(XII)

R' = loweralkyl, methoxymethyl, triloweralkylsilyl

Alternatively, the ether linkage may be introduced during the synthetic sequence described in STEP A above. Thus, the ether linkage may be introduced by reacting compound V with a suitable reagent according to a routine method known in the art.

STEP D

A bromine-substituted ether compound of formula XIIa obtained from STEP. B or STEP C is reacted with an alkyllithium, preferably sec-BuLi in a routine manner known in the art and the resultant lithio compound (without isolation) is allowed to react with an electrophile in a routine manner known in the art to afford a compound of formula XIIb where Z is loweralkyl, —COOH, loweralkoxycarbonyl, formyl or loweralkylaminocarbonyl. Thus, for instance, when Z in formula XIIb is loweralkyl, loweralkyl iodide is used as an electrophile, when it is —COOH, $CO_2$ is used, when it is loweralkoxycarbonyl, loweralkoxycarbonyl chloride is used, when it is formyl, dimethylformamide is used, and when it is loweralkylaminocarbonyl, loweralkylisocyanate is used.

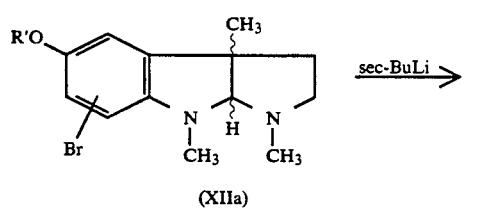

(XIIa)

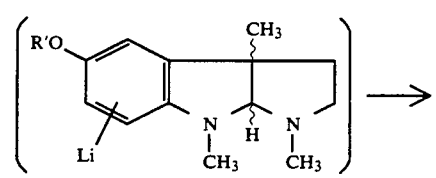

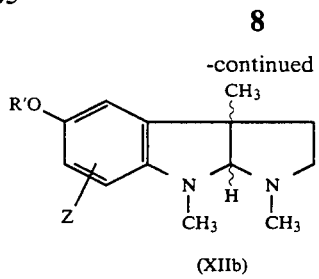

(XIIb)

Z = loweralkyl, —COOH,
loweralkoxycarbonyl,
formyl,
loweralkylaminocarbonyl

STEP E

Compound XI is reacted with an isocyanate of the formula $R_2-N=C=O$ to afford a compound of formula XIII below.

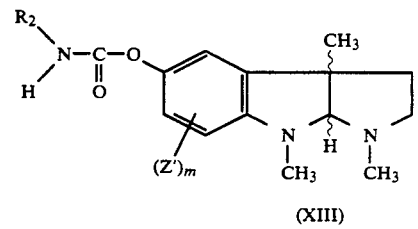

(XIII)

Typically, compound XI and the isocyanate are dissolved in a suitable solvent such as anhydrous tetrahydrofuran which has previously been degassed. Degassing is helpful because compound XI is susceptible to air oxidation. It is also helpful to add a catalytic amount (less than equivalent amount) of sodium metal to the resultant solution in order to facilitate the reaction. Said reaction is usually conducted between room temperature and about 70° C. Reflux condition is particularly convenient.

STEP F

A compound of formula XIV below (where $R_3$ is not hydrogen) is prepared by reacting compound XI with 1,1'-carbonyldiimidazole and thereafter adding a primary or secondary amine of the formula

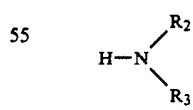

to the solution.

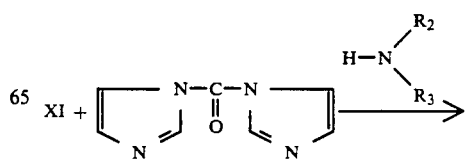

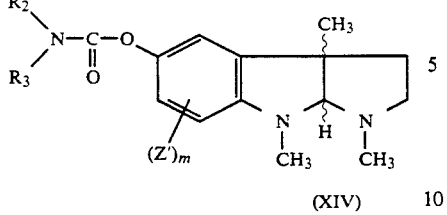

(XIV)

Said reaction between compound XI and 1,1'-carbonyldiimidazole is typically conducted by preparing a degassed solution of compound XI in a suitable solvent such as dichloromethane, adding 1,1'-carbonyldiimidazole to the solution and stirring the solution at room temperature for a suitable length of time such as one hour. Said carbamation reaction is typically conducted by adding the primary or secondary amine

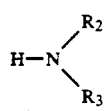

to the solution obtained above and stirring the solution at room temperature for a few hours.

As an alternative to the above reaction route, one can prepare compound XIV by reacting compound XI with a carbamyl chloride of the formula

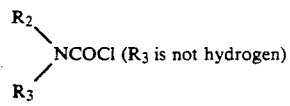

(typically in a degassed solution comprising the reactants, a suitable solvent such as anhydrous dimethylformamide and potassium carbonate, at room temperature), but the former method is much more preferable.

Although the substituent at the 1-position is a methyl group in the reaction depicted above, it will be apparent that said STEP F can be applied to other cases, namely, those where the substituent at the 1-position is loweralkyl, arylloweralkyl, heteroarylloweralkyl, cycloalkylmethyl or loweralkenylmethyl. The same is also true of STEP G described below.

STEP G

A compound of formula XV below is prepared by reacting compound XI with 1,1'-thiocarbonyldiimidazole and thereafter adding a primary or secondary amine

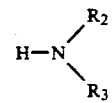

to the solution. This step is conducted in substantially the same manner as in STEP F described above.

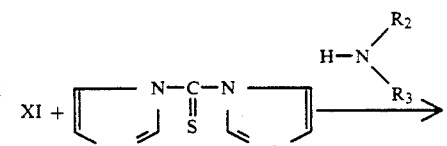

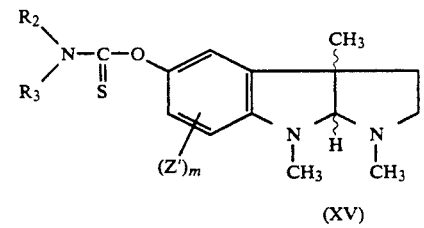

(XV)

As an alternative to the above reaction route, one can prepare compound XV by reacting compound XI with a thiocarbamyl chloride of the formula

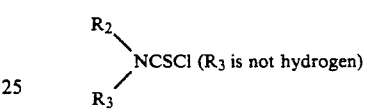

(typically in a degassed solution comprising the reactants, a suitable solvent such as anhydrous dimethylformamide and potassium carbonate, at room temperature), but the former method is much more preferable

STEP H

Instead of relying on STEP A for the introduction of Br or $CH_3$ into the $C_6$-position of the ring system, one can, as a special case, introduce Br or $CH_3$ into the $C_6$-position of compound IIa and obtain compund IIb depicted below (where Z' is Br or $CH_3$) by use of the method described by Sibi and Snieckus, J. Org. Chem., 1983, Volume 48, 1935–1937. Thus, compound IIa is reacted with sec-BuLi and the resultant lithio compound (Li atom at the $C_6$-position) is reacted with bromine or methyl iodide to obtain compound IIb.

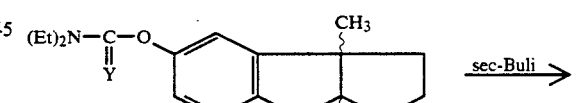

(IIa)

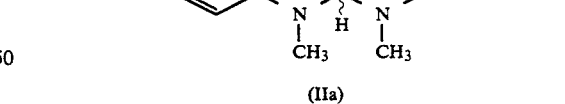

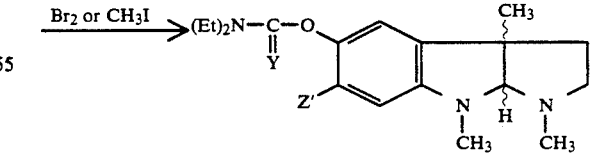

(Z' = Br or $CH_3$)

(IIb)

When the lithio intermediate mentioned above is allowed to react with a triloweralkylsilyl halide, as for instance, trimethylsilyl chloride, a compound of formula IIb where Z' is triloweralkylsilyl is obtained. Said triloweralkylsiyl group may then be replaced via ipso substitution by a variety of electrophiles such as halogens. For details of electrophile-induced desilylation, the reader is referred to E. W. Colvin, "Silicon in Organic Synthesis", Chapter 10, Butterworth, London, 1981.

STEP I

A thiophenolic derivative of formula XVI can be prepared by heating a compound of formula XVa obtained in STEP F. This Newman-Kwart type rearrangement reaction is typically conducted by heating said compound at an elevated temperature, in some cases, of about 150° C. to 300° C. for a few hours.

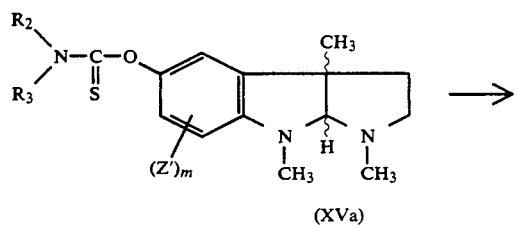

(XVa)

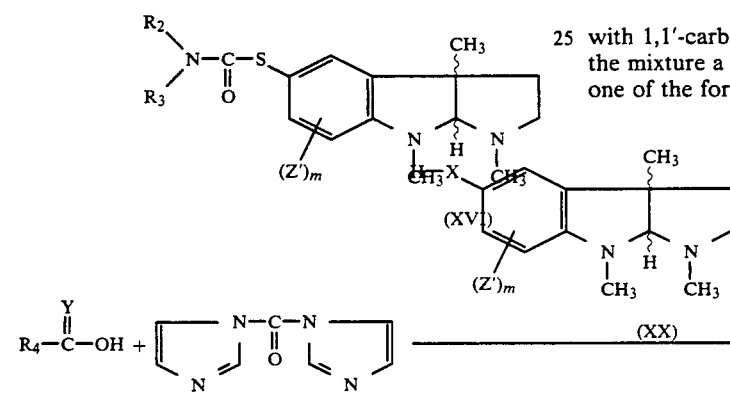

STEP J

A thiophenol compound of formula XVII can be prepared by hydrolyzing compound XVI. Said hydrolysis is typically conducted in a suitable degassed solvent such as ethanol containing sodium hydroxide and by stirring the reaction mixture at room temperature or higher for a few hours.

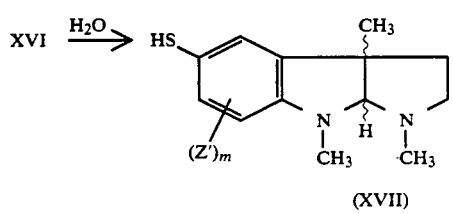

(XVII)

STEP K

Once compounds XVII are obtained, compounds of formula XVIII below can be obtained by utilizing STEPS E through H described above.

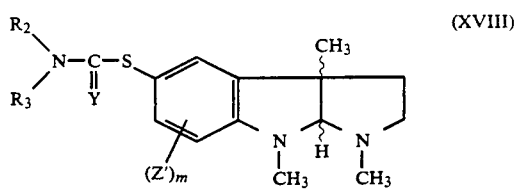

STEP L

A compound of formula XIX can be prepared by reacting a carboxylic acid or thiocarboxylic acid of the formula $$R_4-\overset{Y}{\underset{\|}{C}}-OH$$

with 1,1'-carbonyldiimidazole and thereafter adding to the mixture a compound of formula XX obtained from one of the foregoing steps.

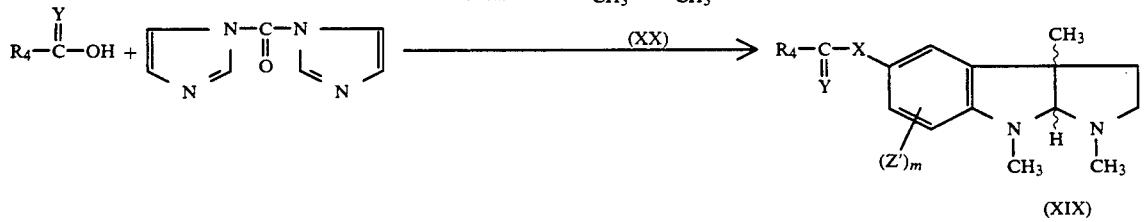

(XIX)

STEP M

In all the products obtained in STEPS B through L, the substituent on the 1-position of the ring is a methyl group. However, the corresponding compounds of formula XXI carrying various substituent groups on the phenyl ring and in which the substituent at 1-position is hydrogen can be prepared by first protecting the amino hydrogen at 1-position with a suitable group and then utilizing one or more of STEPS B through L and thereafter removing the protective group, or alternatively in certain cases by introducing a desired group —X—R or —(Z')$_m$ during the synthetic sequence leading to compound VIII or VIIIa which is described in STEP A. In this manner, one can obtain compounds of formula XXI below

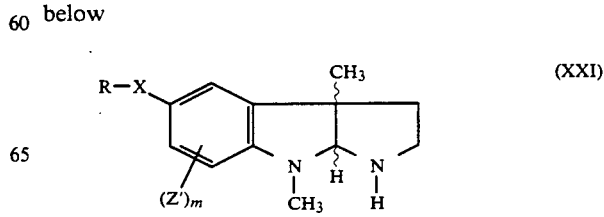

STEP N

A compound of formula XXII can be prepared by reacting a compound of formula XXI with a halide compound of the formula $R_1$—Hal where Hal is Cl, Br or I, (Br or I preferred) and $R_1$ is not hydrogen in a routine manner known in the art.

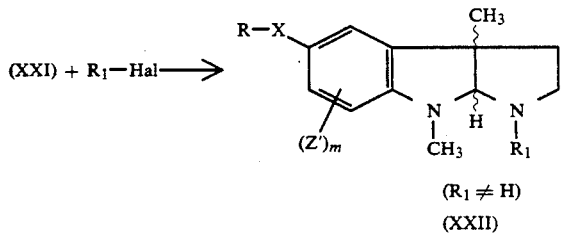

$(XXI) + R_1-Hal \longrightarrow$ $(R_1 \neq H)$
(XXII)

STEP O

A compound of formula I where one or both of the groups $(Z)_m$ are —$NH_2$ can be prepared by reducing the corresponding nitro compound of formula I where one or both of the groups $(Z)_m$ are —$NO_2$ according to a routine manner known to the art.

STEP P

A compound of formula I where one or both of the groups $(Z)_m$ are loweralkylcarbonylamino, arylcarbonylamino, loweralkoxycarbonylamino or loweralkylamino can be prepared by reacting the corresponding amino compound of formula I where one or both of the groups $(Z)_m$ are —$NH_2$ and R is not H with a suitable acylating agent or alkylating agent according to a routine manner known in the art.

The compounds of formula I of the present invention are useful in the treatment of various memory dysfunctions characterized by decreased cholinergic function, such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum AChE) will give rise to fewer side effects and thus lower toxicity than physostigimine (an unspecific AChE inhibitor). We have determined in vitro inhibition of acetylcholinesterase activity in rat striatum and in vitro inhibition of butrylcholinesterase activity in human serum according to the methods described below. Results of some of the compounds of this invention as well as those of physostigmine are presented in Table 1.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinominetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. Pharmacol. 7, 98 (1961).

Procedure

A. Reagents
1. 0.05M Phosphate buffer, pH 7.2
   (a) 6.85 g $NaH_2PO_4 \cdot H_2O/100$ ml distilled $H_2O$
   (b) 13.40 g $Na_2HPO_4 \cdot 7H_2O/100$ ml distilled $H_2O$
   (c) add (a) to (b) until pH reaches 7.2
   (d) Dilute 1:10
2. Chromogen-substrate buffer
   (a) 9.9 mg 5,5-dithiobisnitrobenzoic acid (DTNB) (0.25 mM)
   (b) 99 mg s-acetylthiocholine chloride (5 mM)
   (c) q.s. to 100 ml with 0.05M phosphate buffer, pH 7.2 (reagent 1)
3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine $IC_{50}$ determinations the Abbott Bichromatic Analyzer, ABA-100, is used to determine acetylcholinesterase activity.
Instrument settings
Filter: 450–415
Incubation temperature: 30° C.
Decimal point: 0000.
Analysis time: 5 minutes
Carousel Revolution: 3
Reaction direction:
   down
   endpoint
Syringe plate: 1:101 dilution.

Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with Gilford 250 spectrophotometer. This method is used for more accurate kinetic measurments.

Instrument settings
Lamp: visible
Filter: no filter
Wavelength: 412 nm
Slit width: 0.2 mm
Selection: small aperture
Calibrated absorbance: 1.0 unit full scale
Chart speed: 0.5 cm/min.

Reagents are added to the reference and sample side of a split curvette as follows.

| Reference | Sample |
|---|---|
| 0.8 ml 0.05M phosphate buffer | 0.8 ml 0.05M phosphate buffer |
| 0.8 ml Chromogen-substrate buffer | 0.8 ml Chromogen-substrate buffer |
| | 10 microliter enzyme (tissue homogentate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula $$\text{rate(moles/liter/min)} = \text{slope}/(1.36 \times 10^4).$$

In Vitro Inhibition of Butyrylcholinesterase Activity in Human Serum

This assay can be used in conjunction with the acetylcholinesterase assay to determine the enzyme selectivity of various chloinesterase inhibitors.

Butyrylcholinesterase (BChE), which is sometimes called pseudocholinesterase, preferentially hydrolyzes butyrylcholine. This enzyme is found in the highest amounts in serum, but its physiological role is not known. Ethopropazine and tetraisopropyl pyrophosphoramide (ISO-OMPA) are selective inhibitors of butyrylcholinesterase. An ex vivo experiment with ISO-OMPA has shown that inhibition of butyrylcholinesterase is not correlated with any significant acute chloinomimetic effects.

Procedure

A. Reagents-
1. 0.05M Phosphate buffer, pH 7.2
   (a) 6.85 g $NaH_2PO_4 \cdot H_2O$/100 ml distilled $H_2O$
   (b) 13.40 g $Na_2HPO_4 \cdot 7H_2O$/100 ml distilled $H_2O$
   (c) add (a) to (b) until pH reaches 7.2
   (d) Dilute 1:10
2. Chromogen-substrate buffer
   (a) 9.9 mg 5,5-dithiobisnitrobenzoic acid (DTNB) (0.25 mM)
   (b) 113 mg s-butyrylthiochloine chloride (5 mM)
   (c) q.s. to 100 ml with 0.05M phosphate buffer, pH 7.2 (reagent 1)
3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.
B. Enzyme Preparation
A vial of lyophilized human serum (Precilip, Biodynamics, Houston, Tex. is reconstituted in 3 ml of distilled water. A 10 microliter aliquot of this suspension is added to 90 microliter of the vehicle or various concentrations of the test drug and preincubated for 10 minutes at room temperature.
C. Assay
Substantially the same procedure is used as described above in Section C of the Procedure used for determining the inhibition of acetylcholinsterase activity.

TABLE 1

| Compound | Inhibitory Concentration $(10^{-6}M)$ | |
|---|---|---|
| | Brain AChE | Serum AChE |
| Physostigmine (namely, (3aS-cis)-1,2,3,3a,8,8a-hexahydro-1,3a,8-trimethyl-pyrrolo[2,3-b]indol-5-ol, methyl carbamate ester) | 0.1 | 0.06 |
| (3aS-cis)-1,2,3,3a,8,8a-hexahydro-1,3a,8-trimethyl-pyrrolo[2,3-b]indol-5-ol, cyclohexyl carbamate ester | 0.9 | >1000 |
| (3aS-cis)-1,2,3,3a,8,8a-hexahydro-1,3a,8-trimethyl-pyrrolo[2,3-b]indol-5-ol, [(S*)-(1-phenyl)ethyl]-carbamate ester | 3.1 | >1000 |
| (3aS-cis)-1,2,3,3a,8,8a-hexahydro-1,3a,8-trimethyl-pyrrolo[2,3-b]indol-5-ol, [(R*)-(1-phenyl)ethyl]-carbamate ester | 1.2 | 0.9 |
| (3aS-cis)-1,2,3,3a,8,8a-hexahydro-1,3a,8-trimethyl-pyrrolo[2,3-b]indol-5-ol, 3-chlorophenyl carbamate ester | 0.6 | >1000 |
| (3aS-cis)-1,2,3,3a,8,8a-hexahydro-1,3a,8-trimethylpyrrolo-[2,3-b]indol-5-ol, cyclododecyl carbamate ester | 0.41 | >1000 |
| 3-[3-azabicyclo[3.2.2]nonane] carboxylic acid, (3aS-cis)-1,2,3,3a,8,8a-hexahydro-1,3a,8-trimethylpyrrolo[2,3-b]indol-5-yl ester fumarate | 0.84 | >1000 |
| (3aS-cis)-1,2,3,3a,8,8a-hexahydro-1,3a,8-trimethylpyrrolo-[2,3-b]indol-5-ol, (1-adamantyl) carbamate ester | 3.05 | >100 |
| (3aS-cis)-1,2,3,3a,8,8a-hexahydro-1,3a,7,8-tetramethylpyrrolo-[2,3-b]indol-5-ol, methyl carbamate ester | 0.012 | |

This utility is further demonstrated by the ability of these compounds to restore cholinergically deficient memory in the Dark Avoidance Assay, where they are in general active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

The results of some of the compounds of this invention are presented in Table 2 along with the result of physostigmine.

TABLE 2

| Compound | Dose (mg/kg of body weight, s.c) | % of Animals with Scopolamine Induced Memory Deficit Reversal |
|---|---|---|
| Physostigmine (namely, (3aS-cis)-1,2,3,3a,8,8a-hexahydro-1,3a,8-trimethyl-pyrrolo[2,3-b]indol-5-ol, methyl carbamate ester) | 0.31 | 20% |
| (3aS-cis)-1,2,3,3a,8,8a-hexahydro-1,3a,8-trimethyl-pyrrolo[2,3-b]indol-5-ol, cyclohexyl carbamate ester | 0.16 | 31% |
| (3aS-cis)-1,2,3,3a,8,8a-hexahydro-1,3a,8-trimethyl-pyrrolo[2,3-b]-indol-5-ol, [(S*)-(1-phenyl)ethyl]-carbamate ester | 0.31 | 20% |
| (3aS-cis)-1,2,3,3a,8,8a-hexahydro-1,3a,8-trimethyl-pyrrolo[2,3-b]indol-5-ol, [(R*)-(1-phenyl)ethyl]-carbamate ester | 1.25 | 67% |
| (3aS-cis)-1,2,3,3a,8,8a-hexahydro-1,3a,8-trimethyl-pyrrolo[2,3-b]indol-5-ol, (4-pyridinyl)carbamate ester | 0.31 | 27% |
| (3aS-cis)-1,2,3,3a,8,8a-hexahydro-1,3a,8-trimethyl-pyrrolo[2,3-b]indol-5-ol, 3-chlorophenyl carbamate ester | 5.00 | 20% |
| 3-[3-azabicylclo[3.2.2]nonane] carboxylic acid, (3aS-cis)-1,2,3,3a,8,8a-hexahydro-1,3a,8-trimethylpyrrolo[2,3-b]indol-5-yl ester fumarate | 5.00 | 33% |
| (3aS-cis)-1,2,3,3a,8,8a-hexahydro-1,3a,8-trimethylpyrrolo[2,3-b]indol-5-ol, (1-adamantyl) carbamate ester | 1.25 | 27% |
| (3aS-cis)-6-bromo-1,2,3,3a,8,8a-hexahydro-1,3a,8-trimethylpyrrolo[2,3-b]indol-5-ol, N,N-diethylcarbamate ester | 5.00 | 40% |

Additionally, some of the compounds of this invention exhibit antidepressant activities, which activities being particularly helpful for patients suffering from Alzheimer's disease. The antidepressant activities were evaluated in this invention on the basis of prevention of tetrabenazine-induced ptosis in mice, yohimbine toxicity potentiation and inhibition of $^3$H-norepinephrine uptake. The test methods and results are described below.

Prevention of Tetrabenazine-Induced Ptosis In Mice

Tetrabenazine (TBZ) induces behavioral depression with concomitant ptosis in mice similar to reserpine. Antidepressant compounds, both monoamineoxidase inhibitors and tricyclics, are known to prevent or antagonize these effects and the degree of antagonism correlates with clinical efficacy. The prevention of TBZ-induced ptosis in mice is used as a preliminary screen for possible antidepressant activity. The method used in this invention is as follows:

Male mice weighing 20 to 30 grams are used in test groups of five subjects. All compounds are dissolved or suspended with a suitable surfactant in distilled water and administered in volumes of 10 ml/kg of body weight. TBZ solution is made from the methanesulfonate salt and the concentration is adjusted to enable administration of 60 mg/kg of base by intraperitoneal (i.p.) injection.

The pretreatment time is measured from the time of dosing to observation. Therefore, when a 30-minute pretreat is utilized, drug and TBZ are given simultaneously. A control group receives solvent and TBZ at intervals identical to drug group. For a primary screen, the drug is administered i.p. and a group size of five is utilized. Eight animals/group are used for a dose range.

Thirty minutes after TBZ, the subjects are placed in individual plastic containers (10.5×8×6 inches) in the presence of white noise and one minute after the transfer, they are scored for ptosis on the following scale: Eyes closed=4, eyes ¾ closed=3, eyes ½ closed=2, eyes ¼ closed=1, eyes open=0. The total score for each group of five in a primary screen will, therefore, be from 0 to 20 and these scores are used as indications of drug activity.

The vehicle control group score is used as a determinant of the validity of each test. If the control score is less than 17, the results are discarded and the test repeated. The calculation of percent inhibition of ptosis is:

$$\frac{(\text{Control Score} - \text{Drug Score})}{\text{Control Score}} \times 100\%$$

For ED$_{50}$ estimation, four or five doses are administered in order to bracket the estimated value and only vehicle control scores of 27 to 32 are accepted to assure the accuracy of the ED$_{50}$ estimation.

Linear regression analysis is used to estimate ED$_{50}$ values and 95% confidence intervals.

The results of some of the compounds of this invention are shown in Table 3.

Yohimbine Toxicity Potentiation

The potentiation of yohimbine toxicity is considered an additional test for screening antidepressant drugs. The method used in this invention is as follows:

Male mice weighing 20 to 30 grams are used. They are housed under standard laboratory conditions with free access to food and water. Compounds are dissolved in distilled water and a suitable surfactant is added in case of poor solubility. Yohimbine hydrochloride is dissolved in distilled water as well. Both compound and yohimbine are administered in a volume of 10 mg/kg.

Compounds and vehicle are administered orally 60 minutes prior to a sublethal dose (30 mg/kg s.c.) of yohimbine hydrochloride which alone causes death in about 1% of mice (4 out of 400). Ten mice per group are then placed in plastic cages (26×10×16 cm) with food and water available ad libitum. Mortality rate is assessed 18 hours postdosing. ED$_{50}$ is defined as dose of drug causing death in 5/10 mice and is calculated by probit analysis. The results of some of the compounds of this invention are presented in Table 3.

TABLE 3

| Compound | % Inhibition @ Dose (mg/kg) | |
|---|---|---|
| | TBZ | YTP |
| (3aS-cis)-1,2,3,3a,8,8a-hexahydro-1,3a,8-trimethyl-pyrrolo[2,3-b]indol-5-ol, cyclohexyl carbamate ester | 20% @ 1.25 | — |
| (3aS-cis)-1,2,3,3a,8,8a-hexahydro-1,3a,8-trimethyl-pyrrolo[2,3-b]indol-5-ol, [(S*)-(1-phenyl)ethyl]-carbamate ester | 35% @ 20 | $ED_{50} = 30$ |
| (3aS-cis)-1,2,3,3a,8,8a-hexahydro-1,3a,8-trimethyl-pyrrolo[2,3-b]indol-5-ol, [(R*)-(1-phenyl)ethyl]-carbamate ester | 50% @ 20 | $ED_{50} = 16.1$ |
| (3aS-cis)-1,2,3,3a,8,8a-hexahydro-1,3a,8-trimethyl-pyrrolo[2,3-b]indol-5-ol, 3-chlorophenyl carbamate ester | 45% @ 60 | 63% @ 80 |

$^3$H-Norepinephrine Uptake in Rat Whole Brain or Hypothalamic Synaptosomes

This assay is used as a biochemical screen for potential antidepressants which block norepinephrine uptake.

The neuronal re-uptake mechanism for norepinephrine (NE) is the most important physiological means for inactivating NE by removing the transmitter from the synaptic cleft. NE uptake is accomplished by a saturable, stereospecific, high-affinity ($K_m = 10^{-7}$-$10^{-6}$M), sodium-dependent, active transport system, which has been shown to exist in both peripheral and central nervous system tissues, using slice, homogenate and purified synaptosome preparations. NE uptake is potently inhibited by cocaine, phenethylamines and tricyclic antidepressants. It is also inhibited by ouabain, metabolic inhibitors and phenoxybenzamine. The inhibition of NE uptake by clinically effective tricyclic antidepressants is an important link in the catecholamine hypothesis of affective disorders.

There are large regional variations in NE uptake which correlate with the endogenous levels of NE. The hypothalamus shows the highest level of NE and the greates uptake. This region is used for further testing of compounds showing activity in whole brain preparations.

Synaptosomal $^3$H-NE uptake is a useful marker for the integrity of noradrenergic neurons, after lesioning experiments, as well as an assay for compounds which potentiate the action of NE by blocking the reuptake mechanism.

Procedure

A. Animals: Male CR Wistar rats (100–125 g).
B. Reagents
1. Krebs-Henseleit Bicarbonate Buffer, pH 7.4 (KHBB). Make a 1 liter batch, containing the following salts.

| | grams/L | mM |
|---|---|---|
| NaCl | 6.92 | 118.4 |
| KCL | 0.35 | 4.7 |
| $MgSO_4.7H_2O$ | 0.29 | 1.2 |
| $KH_2PO_4$ | 0.16 | 2.2 |
| $NaHCO_3$ | 2.10 | 24.9 |
| $CaCl_2$ | 0.14 | 1.3 |

-continued

| | grams/L | mM |
|---|---|---|
| Prior to use add: | | |
| Dextrose | 2 mg/ml | 11.1 |
| Iproniazid phosphate | 0.30 mg/ml | 0.1 |

Aerate for 60 min. with 95% $O_2$/5% $CO_2$, check pH (7.4±0.1).

2. 0.32M Sucrose: 21.9 g of sucrose, q.s. to 200 ml.
3. L(—)-Norepinephrine bitartrate is procured from a commercial source. A 0.1 mM stock solution is made up in 0.01N HCl. This is used to dilute the specific activity of the radiolabeled NE.
4. Levo-[Ring-2,5,6-$^3$H]-Norepinephrine (40–50 Ci/mmol) is obtained from a commercial source. The final desired concentration of $^3$H-NE in the assay is 50 nM. The dilution factor is 0.8; therefore the KHBB is made up to contain 62.5 nM [$^3$H]-NE.
Add to 100 ml og KHBB:

| A. 59.4 microliter of 0.1 mM NE = | 59.4 nM |
|---|---|
| B. 0.31 nmole of $^3$H—NE = | 3.1 nM |
| | 62.5 nM |

5. For most assays, a 1 mM stock solution of the test compound is made up in a suitable solvent and serially diluted such that the final concentration in the assay ranges from $2 \times 10^{-8}$ to $2 \times 10^{-5}$ M. Seven concentrations are used for each assay. Higher or lower concentrations may be used depending on the potency of the test compound.

C. Tissue Preparation

Male Wister rats are decapitated and brains rapidly removed. Either whole brain minus cerebella or hypothalamus is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 min at 0°–4° C. The supernatant ($S_1$) is decanted and is used for uptake experiments.

D. Assay

| 800 microliter | KHBB containing [$^3$H]—NE |
| 20 microliter | Vehicle or appropriate drug concentration |
| 200 microliter | Tissue suspension |

Tubes are incubated at 37° C. under 95% $O_2$/5% $CO_2$ atmosphere for five minutes. For each assay, 3 tubes are incubated with 20 microliters of vehicle at 0° C. in an ice bath. After incubation all tubes are immediately centrifuged at 4000 g for ten minutes. The supernatant fluid is aspirated and the pellets dissolved by adding 1 ml of a solubilizer. The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

The results of some of the compounds of this invention are presented in Table 4 along with the result for physostigmine.

TABLE 4

| Compound | Reuptake Inhibition (10⁻⁶M) of neurotransmitters Norepinephrine |
|---|---|
| Physostigmine (namely, (3aS-cis)-1,2,3,3a,8,8a-hexahydro-1,3a,8-trimethyl-pyrrolo[2,3-b]indol-5-ol, methyl carbamate ester) | >20 |
| (3aS-cis)-1,2,3,3a,8,8a-hexahydro-1,3a,8-trimethyl-pyrrolo[2,3-b]indol-5-ol, 4-ethylcyclohexyl carbamate ester | 2.6 |
| (3aS-cis)-1,2,3,3a,8,8a-hexahydro-1,3a,8-trimethyl-pyrrolo[2,3-b]-indol-5-ol, [(S*)-(1-phenyl)ethyl]-carbamate ester | 2.2 |
| (3aS-cis)-1,2,3,3a,8,8a-hexahydro-1,3a,8-trimethyl-pyrrolo[2,3-b]indol-5-ol, [(R*)-(1-phenyl)ethyl]-carbamate ester | 12 |
| (3aS-cis)-1,2,3,3a,8,8a-hexahydro-1,3a,8-trimethyl-pyrrolo[2,3-b]indol-5-ol, (4-pyridinyl)carbamate ester | >20 |
| (3aS-cis)-1,2,3,3a,8,8a-hexahydro-1,3a,8-trimethyl-pyrrolo[2,3-b]indol-5-ol, 3-chlorophenyl carbamate ester | 1.8 |

Furthermore, the compounds of this invention are in general less toxic than heretofore known compounds such as tacrine and physostigmine, making them therapeutically more acceptable.

$LD_{50}$ is determined by the dose (mg/kg) at which 50% of the test animals die within 24 hours. In many cases this dose is an approximation. The results of some of the compounds of this invention are presented in Table 5 along with the result for physostigmine.

TABLE 5

| Compound | $LD_{50}$ (mg/kg, i.p.) |
|---|---|
| Physostigmine (namely, (3aS-cis)-1,2,3,3a,8,8a-hexahydro-1,3a,8-trimethyl-pyrrolo[2,3-b]indol-5-ol, methyl carbamate ester) | ≈3 |
| (3aS-cis)-1,2,3,3a,8,8a-hexahydro-1,3a,8-trimethyl-pyrrolo[2,3-b]indol-5-ol, cyclohexyl carbamate ester | >5 <10 |
| (3aS-cis)-1,2,3,3a,8,8a-hexahydro-1,3a,8-trimethyl-pyrrolo[2,3-b]-indol-5-ol, [(S*)-(1-phenyl)ethyl]-carbamate ester | >40 <80 |
| (3aS-cis)-1,2,3,3a,8,8a-hexahydro-1,3a,8-trimethyl-pyrrolo[2,3-b]indol-5-ol, [(R*)-(1-phenyl)ethyl]-carbamate ester | ≈40 |
| (3aS-cis)-1,2,3,3a,8,8a-hexahydro-1,3a,8-trimethyl-pyrrolo[2,3-b]indol-5-ol, (4-pyridinyl)carbamate ester | ≈40 |
| (3aS-cis)-1,2,3,3a,8,8a-hexahydro-1,3a,8-trimethyl-pyrrolo[2,3-b]indol-5-ol, 3-chlorophenyl carbamate ester | >80 |

Compounds I of the present invention are also useful as analgesic agents due to their ability to alleviate pain in mammals. The activity of the compounds is demonstrated in the 2-phenyl-1,4-benzoquinone-induced writhing (PQW) test in mice, a standard assay for analgesic [Proc. Soc. Exptl. Biol. Med., 95,729 (1957)] and in modified Haffner's analgesia.

The latter assay is used to evaluate analgesic activity by measuring drug-induced changes in the sensitivity of mice to pressure stress by placing an artery clip (2½ inches long) on their tail. The procedure used is a modification of the test developed by Haffner, Dtsch. Med. Wschr., 55, 731 (1929), and it is described below.

METHOD

Male mice (Charles River, CD-1) from 18–30 grams are used for the test. An artery clip is applied to the root of the tail of a mouse (approximately ½ inch from the body) to induce pain. The animal quickly responds to this noxious stimuli by biting the clip or the location of the clip. This reaction time, the interval between stimulus onset and response, is recorded in 1/10-second increments by a stop watch.

For a time response, the screening dose (25 mg/kg) is administered subcutaneously (10 ml/kg) to the animal receiving food and water ad libitum before testing. Animals receiving the compound orally are fasted 18–24 hours before drug administration. Drug to be tested is prepared with distilled water and if insoluble, one drop of a surfactant is added.

Twenty-eight animals (seven/group) are administered the drug 15, 30, 45 and 60 minutes prior to testing.

The cut-off time (CO) is determined by taking the ($\bar{x}$) average +(3) standard (SD) deviations of the combined response latencies of the control mice in all time periods.

Listed in Table 6 are test results of the analgesic activities of a compound of this invention along with those of eseroline salicylate used as a reference compound. As compared with eseroline, the compounds of this invention are much less toxic, have a longer lasting analgesic effect, have less physical dependence liability and are more stable.

$$CO = \bar{x} + 3\ SD\ (seconds)$$

Any reaction time, in subsequent drug tests, which is greater than the CO (for the same time period) therefore exceeds 99% of a normal Gaussian distribution and is called "positive response" indicative of analgesic activity. A time response indicates the period of greatest analgesic effect after dosing. The $ED_{50}$ is determined at the peak time of drug activity. A minimum of three dose groups are used. $ED_{50}$'s are calculated using computer analysis.

TABLE 6

| | ANALGESIC ACTIVITY ($ED_{50}$) | |
|---|---|---|
| Compound | PQW | Modified Haffner's Analgesia |
| (3aS-cis)-7-bromo-1,2,3,3a,8,8a-hexahydro-1,3a,8-trimethylpyrrolo[2,3-b]indol-5-ol | 0.041 mg/kg,sc 0.36 mg/kg,po | 0.55 mg/kg,sc |
| (3aS-cis)-7-bromo-1,2,3,3a,8,8a-hexahydro-1,3a,8-trimethylpyrrolo[2,3-b]indol-5-ol, trimethylacetate ester hydrochloride | 0.8 mg/kg,sc | 0.6 mg/kg,sc |
| 7-bromo-1,2,3,3a,8,8a-hexahydro-1,3a,8-trimethylpyrrolo- | 0.17 mg/kg,sc 0.33 mg/kg,po | 0.22 mg/kg,sc |

TABLE 6-continued

ANALGESIC ACTIVITY (ED$_{50}$)

| Compound | PQW | Modified Haffner's Analgesia |
|---|---|---|
| [2,3-b]indol-5-ol (3aS-cis)-1,2,3,3a,8,8a-hexahydro-7-nitro-1,3a,8-trimethylpyrrolo-[2,3-b]indol-5-ol acetate ester fumarate | 1.50 mg/kg,sc | 3.60 mg/kg,sc |
| (3aS-cis)-1,2,3,3a,8,8a-hexahydro-1,3a,7,8-tetramethylpyrrolo-[2,3-b]indol-5-ol | 0.22 mg/kg,sc | 0.31 mg/kg,sc |
| 1,2,3,3a,8,8a-hexahydro-3a,8-dimethyl-1-(2-propenyl)pyrrolo[2,3-b]-indol-5-ol salicylate | 3.90 mg/kg,sc | 2.56 mg/kg,sc |
| 7-bromo-1-ethyl-1,2,3,3a,8,8a-hexahydro-3a,8-dimethylpyrrolo[2,3-b]-indol-5-ol salicylate | 2.52 mg/kg,sc | 1.94 mg/kg, sc |
| eseroline salicylate (reference compound) | 0.52 mg/kg,sc | 0.18 mg/kg,sc |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include those listed below as well as the 3aR-cis isomers thereof and mixtures of the 3aS-cis and 3aR-cis isomers including the racemic mixtures:

(3aS-cis)-1,2,3,3a,8,8a-hexahydro-1,3a,8-trimethylpyrrolo[2,3-b]indol-5-ol, octadecyl carbamate ester;

(3aS-cis)-7-chloro-1,2,3,3a,8,8a-hexahydro-1,3a,8-trimethylpyrrolo[2,3-b]indol-5-ol, methyl carbamate ester;

(3aS-cis)-7-bromo-1,2,3,3a,8,8a-hexahydro-1,3a,8-trimethylpyrrolo[2,3-b]indol-5-ol, methyl carbamate ester;

(3aS-cis)-1,2,3,3a,8,8a-hexahydro-1,3a,8-trimethylpyrrolo[2,3-b]indol-5-ol, N,N-diethyl carbamate ester;

(3aS-cis)-1,2,3,3a,8,8a-hexahydro-1,3a,8-trimethylpyrrolo[2.3-b]indol-5-ol, cyclopentylmethyl carbamate ester;

(3aS-cis)-1,2,3,3a,8,8a-hexahydro-1,3a,8-trimethylpyrrolo[2,3-b]indol-5-ol, (thien-3-yl)methyl carbamate ester;

(3aS-cis)-1,2,3,3a,8,8a-hexahydro-1,3a,8-trimethylpyrrolo[2,3-b]indol-5-ol, benzyl carbamate ester;

(3aS-cis)-1,2,3,3a,8,8a-hexahydro-1,3a,8-trimethylpyrrolo[2,3-b]indol-5-ol, (2-phenyl)ethyl carbamate ester;

(3aS-cis)-1,2,3,3a,8,8a-hexahydro-1,3a,8-trimethylpyrrolo[2,3-b]indol-5-ol, [(S*)-(1-phenyl)ethyl]carbamate ester;

(3aS-cis)-1,2,3,3a,8,8a-hexahydro-1,3a,8-trimethylpyrrolo[2,3-b]indol-5-ol, [(R*)-(1-phenyl)ethyl]carbamate ester;

(3aS-cis)-7-chloro-1,2,3,3a,8,8a-hexahydro-1,3a,8-trimethylpyrrolo[2,3-b]indol-5-ol, [(S*)-(1-phenyl)ethyl]carbamate ester;

(3aS-cis)-7-bromo-1,2,3,3a,8,8a-hexahydro-1,3a,8-trimethylpyrrolo[2,3-b]indol-5-ol, [(S*)-(1-phenyl)ethyl]-carbamate ester;
(3aS-cis)-1,2,3,3a,8,8a-hexahydro-1,3a,8-trimethylpyrrolo[2,3-b]indol-5-ol, [1-(1-naphthyl)ethyl]carnamate ester;
(3aS-cis)-1,2,3,3a,8,8a-hexahydro-1,3a,8-trimethylpyrrolo[2,3-b]indol- 5-ol, cyclohexyl carbamate ester;
(3aS-cis)-7-chloro-1,2,3,3a,8,8a-hexahydro-1,3a,8-trimethylpyrrolo[2,3-b]indol-5-ol, cyclohexyl carbamate ester;
(3aS-cis)-7-bromo-1,2,3,3a,8,8a-hexahydro-1,3a,8-trimethylpyrrolo[2,3-b]indol-5-ol, cyclohexyl carbamate ester;
(3aS-cis)-1,2,3,3a,8,8a-hexahydro-1,3a,8-trimethylpyrrolo[2,3-b]indol-5-ol, 4,4-dimethylcyclohexyl carbamate ester;
(3aS-cis)-1,2,3,3a,8,8a-hexahydro-1,3a,8-trimethylpyrrolo[2,3-b]indol-5-ol, 4-ethylcyclohexyl carbamate ester;
(3aS-cis)-1,2,3,3a,8,8a-hexahydro-1,3a,8-trimethylpyrrolo[2,3-b]indol-5-ol, spiro[5.5]undecan-3-yl carbamate ester;
(3aS-cis)-1,2,3,3a,8,8a-hexahydro-1,3a,8-trimethylpyrrolo[2,3-b]indol-5-ol, cycloheptyl carbamate ester;
(3aS-cis)-1,2,3,3a,8,8a-hexahydro-1,3a,8-trimethylpyrrolo[2,3-b]indol-5-ol, 1,2-dimethylcyclohexen-4-yl carbamate ester;
(3aS-cis)-1,2,3,3a,8,8a-hexahydro-1,3a,8-trimethylpyrrolo[2,3-b]indol-5-ol, cyclohexen-1-yl carbamate ester;
(3aS-cis)-1,2,3,3a,8,8a-hexahydro-1,3a,8-trimethylpyrrolo[2,3-b]indol-5-ol, bicyclo[2.2.1]heptan-2-yl carbamate ester;
(3aS-cis)-1,2,3,3a,8,8a-hexahydro-1,3a,8-trimethylpyrrolo[2,3-b]indol-5-ol, 3-chlorophenyl carbamate ester;
(3aS-cis)-1,2,3,3a,8,8a-hexahydro-1,3a,8-trimethylpyrrolo[2,3-b]indol-5-ol, 4-chlorophenyl carbamate ester;
(3aS-cis)-1,2,3,3a,8,8a-hexahydro-1,3a,8-trimethylpyrrolo[2,3-b]indol-5-ol, 2,6-dimethylphenyl carbamate ester;
(3aS-cis)-1,2,3,3a,8,8a-hexahydro-1,3a,8-trimethylpyrrolo[2,3-b]indol-5-ol, 4-nitrophenyl carbamate ester;
(3aS-cis)-1,2,3,3a,8,8a-hexahydro-1,3a,8-trimethylpyrrolo[2,3-b]indol-5-ol, 4-pyridinyl carbamate ester;
(3aS-cis)-1,2,3,3a,8,8a-hexahydro-1,3a,8-trimethylpyrrolo[2,3-b]indol-5-ol, 4-methyl-piperazin-1-yl carbamate ester;
(3aS-cis)-1,2,3,3a,8,8a-hexahydro-1,3a,8-trimethylpyrrolo[2,3-b]indol-5-ol, 4-morpholinyl carbamate ester;
(3aS-cis)-1,2,3,3a,8,8a-hexahydro-1,3a,8-trimethylpyrrolo[2,3-b]indol-5-ol, 4-morpholinyl thiocarbamate ester;
(3aS-cis)-1,2,3,3a,8,8a-hexahydro-1,3a,8-trimethylpyrrolo[2,3-b]indol-5-ol, 2-(2,6-dichlorophenylimino)-1-imidazolidinyl carbamate ester;
(3aS-cis)-1,2,3,3a,8,8a-hexahydro-1,3a,8-trimethylpyrrolo[2,3-b]indol-5-ol, 3-chlorophenyl carbamate ester;
(3aS-cis)-7-acetylamino-1,2,3,3a,8,8a-hexahydro-1,3a,8-trimethylpyrrolo[2,3-b]indol-5-ol, 3-chlorophenyl carbamate ester;
(3aS-cis)-6-bromo-1,2,3,3a,8,8a-hexahydro-1,3a,8-trimethylpyrrolo[2,3-b]indol-5-ol, 3-chlorophenyl carbamate ester;
(3aS-cis)-7-bromo-1,2,3,3a,8,8a-hexahydro-1,3a,8-trimethylpyrrolo[2,3-b]indol-5-ol, n-heptyl carbamate ester;
(3aS-cis)-1,2,3,3a,8,8a-hexahydro-1,3a,8-trimethyl-7-nitropyrrolo[2,3-b]indol-5-ol, [(S*)-(1-phenyl)ethyl]-carbamate ester;
(3aS-cis)-7-bromo-1,2,3,3a,8,8a-hexahydro-5-methoxy-1,3a,8-trimethylpyrrolo[2,3-b]indole;
(3aS-cis)-7-chloro-1,2,3,3a,8,8a-hexahydro-5-methoxy-1,3a,8-trimethylpyrrolo[2,3-b]indole;
(3aS-cis)-7-acetylamino-1,2,3,3a,8,8a-hexahydro-5-methoxy-1,3a,8-trimethylpyrrolo[2,3-b]indole;
(3aS-cis)-1,2,3,3a,8,8a-hexahydro-5-methoxy-7-nitro-1,3a,8-trimethylpyrrolo[2,3-b]indole;
(3aS-cis)-7-bromo-1-cyclopropylmethyl-1,2,3,3a,8,8a-hexahydro-5-methoxy-3a, 8-dimethylpyrrolo[2,3-b]indole;
(3aS-cis)-7-bromo-1,2,3,3a,8,8a-hexahydro-5-methoxy-1-(2-phenylethyl)-3a,8-dimethylpyrrolo[2,3-b]indole;
(3aS-cis)-7-bromo-1,2,3,3a,8,8a-hexahydro-5-methoxy-1-(2-propenyl)-3,8a-dimethylpyrrolo[2,3-b]indole;
(3aS-cis)-7-bromo-1-(2-butenyl)-1,2,3,3a,8,8a-hexahydro-5-methoxy-3,8a-dimethylpyrrolo[2,3-b]indole;
(3aS-cis)-7-bromo-1-cyclopropylmethyl-1,2,3,3a,8,8a-hexahydro-3a,8-dimethylpyrrolo[2,3-b]indol-5-ol;
(3aS-cis)-7-bromo-1,2,3,3a,8,8a-hexahydro-1-(2-phenylethyl)-3a,8-dimethylpyrrolo[2,3-b]indol-5-ol;
(3aS-cis)-7-bromo-1,2,3,3a,8,8a-hexahydro-1-(2-propenyl)-3a,8-dimethylpyrrolo[2,3-b]indol-5-ol;
(3aS-cis)-7-bromo-1-(2-butenyl)-1,2,3,3a,8,8a-hexahydro-3a,8-dimethylpyrrolo[2,3-b]indol-5-ol;
(3aS-cis)-1-cyclopropylmethyl-1,2,3,3a,8,8a-hexahydro-7-nitro-3a,8-dimethylpyrrolo[2,3-b]indol-5-ol;
(3aS-cis)-1,2,3,3a,8,8a-hexahydro-7-nitro-1-(2-propenyl)-3a,8-dimethylpyrrolo[2,3-b]indol-5-ol;;
(3aS-cis)-1-(2-butenyl)-1,2,3,3a,8,8a-hexahydro-7-nitro-3a,8-dimethylpyrrolo[2,3-b]indol-5-ol;
(3aS-cis)-1,2,3,3a,8,8a-hexahydro-7-nitro-1-(2-phenylethyl)-3a,8-dimethylpyrrolo[2,3-b]indol-5-ol;
(3aS-cis)-7-bromo-1,2,3,3a,8,8a-hexahydro-1,3a,8-trimethylpyrrolo[2,3-b]indol-5-ol, acetate;
(3aS-cis)-1,2,3,3a,8,8a-hexahydro-7-nitro-1,3a,8-trimethylpyrrolo[2,3-b]indol-5-ol, acetate;
(3aS-cis)-1,2,3,3a,8,8a-hexahydro-7-nitro-1,3a,8-trimethylpyrrolo[2,3-b]indol-5-ol, trimethylacetate;
(3aS-cis)-7-bromo-1,2,3,3a,8,8a-hexahydro-1,3a,8-trimethylpyrrolo[2,3-b]indol-5-ol, heptanoate;
(3aS-cis)-1,2,3,3a,8,8a-hexahydro-7-nitro-1,3a,8-trimethylpyrrolo[2,3-b]indol-5-ol, heptanoate;
(3aS-cis)-7-amino-1,2,3,3a,8,8a-hexahydro-1,3a,8-trimethylpyrrolo[2,3-b]indol-5-ol, methyl carbamate ester;
7-bromo-1,2,3,3a,8,8a-hexahydro-3a,8-dimethylpyrrolo[2,3-b]indol-5-ol;
7-bromo-1,2,3,3a,8,8a-hexahydro-5-methoxy-1,3a,8-trimethylpyrrolo[2,3-b]indole;
7-bromo-1,2,3,3a,8,8a-hexahydro-1,3a,8-trimethylpyrrolo[2,3-b]indol-5-ol;
7-bromo-1-ethyl-1,2,3,3a,8,8a-hexahydro-5-methoxy-3a,8-dimethylpyrrolo[2,3-b]indole;
7-bromo-1-ethyl-1,2,3,3a,8,8a-hexahydro-3a,8-dimethylpyrrolo[2,3-b]-indol-5-ol;
7-bromo-1,2,3,3a,8,8a-hexahydro-5-methoxy-3a,8-dimethyl-1-propylpyrrolo[2,3-b]indole;
7-bromo-1,2,3,3a,8,8a-hexahydro-3a,8-dimethyl-1-propylpyrrolo[2,3-b]indol-5-ol;
1,2,3,3a,8,8a-hexahydro-5-methoxy-3a,8-dimethyl-1-(2-propenyl)pyrrolo[2,3-b]indole;

1,2,3,3a,8,8a-hexahydro-3a,8-dimethyl-1-(2-propenyl)-pyrrolo[2,3-b]indol-5-ol;
7-bromo-1,2,3,3a,8,8a-hexahydro-5-methoxy-1-(2-propenyl)pyrrolo[2,3-b]indole;
1,2,3,3a,8,8a-hexahydro-5-methoxy-3a,8-dimethyl-1-(3-methyl-2-butenyl)pyrrolo[2,3-b]indole;
7-bromo-1,2,3,3a,8,8a-hexahydro-5-methoxy-3a,8-dimethyl-1-(3-methyl-2-butenyl)pyrrolo[2,3-b]indole;
7-bromo-1,2,3,3a,8,8a-hexahydro-1,3a,8-dimethyl-(3-methyl-2-butenyl)pyrrolo[2,3-b]indol-5-ol;
1-cyclopropylmethyl-1,2,3,3a,8,8a-hexahydro-5-methoxy-3a,8-dimethylpyrrolo[2,3-b]indole;
1-cyclopropylmethyl-1,2,3,3a,8,8a-hexahydro-3a,8-dimethylpyrrolo[2,3-b]indol-5-ol;
1-cyclopropylmethyl-1,2,3,3a,8,8a-hexahydro-3a,8-dimethylpyrrolo[2,3-b]indol-5-ol, methyl carbamate ester;
7-bromo-1-cyclopropylmethyl-1,2,3,3a,8,8a-hexahydro-5-methoxy-3a,8-dimethylpyrrolo[2,3-b]indole;
7-bromo-1-(cyclopropylmethyl)-1,2,3,3a,8,8a-hexahydro-3a,8-dimethylpyrrolo[2,3-b]indol-5-ol;
1,2,3,3a,8,8a-hexahydro-5-methoxy-3a,8-dimethyl-1-(2-phenylethyl)-pyrrolo[2,3-b]indole;
1,2,3,3a,8,8a-hexahydro-3a,8-dimethyl-1-(2-phenylethyl)pyrrolo-[2,3-b]indol-5-ol;
1,2,3,3a,8,8a-hexahydro-3a,8-dimethyl-1-(2-phenylethyl)pyrrolo[2,3-b]indol-5-ol, methyl carbamate ester;
7-bromo-1,2,3,3a,8,8a-hexahydro-5-methoxy-3a,8-dimethyl-1-(2-phenylethyl)pyrrolo[2,3-b]indole;
7-bromo-1,2,3,3a,8,8a-hexahydro-3a,8-dimethyl-1-(2-phenylethyl)pyrrolo[2,3-b]indol-5-ol;
(3aS-cis)-1,2,3,3a,8,8a-hexahydro-1,3a,7,8-tetramethylpyrrol[2,3-b]indol-5-ol;
(3aS-cis)-7-bromo-1,2,3,3a,8,8a-hexahydro-5-methoxy-1,3a,8-trimethylpyrrolo[2,3-b]indole;
(3aS-cis)-1,2,3,3a,8,8a-hexahydro-5-methoxy-7-nitro-1,3a,8-trimethylpyrrolo[2,3-b]indole;
(3aS-cis)-1,2,3,3a,8,8a-hexahydro-1,3a,7,8-tetramethylpyrrolo[2,3-b]indol-5-ol, methyl carbamate ester;
(3aS-cis)-1,2,3,3a,8,8a-hexahydro-1,3a,6,8-tetramethylpyrrolo[2,3-b]indol-5-ol, N,N-diethylcarbamate ester;
(3aS-cis)-6-chloro-1,2,3,3a,8,8a-hexahydro-1,3a,8-trimethylpyrrolo[2,3-b]indol-5-ol, N,N-diethyl carbamate ester;
(3aS-cis)-6-bromo-1,2,3,3a,8,8a-hexahydro-1,3a,8-trimethylpyrrolo[2,3-b]indol-5-ol, N,N-diethyl carbamate ester;
(3aS-cis)-7-bromo-1,2,3,3a,8,8a-hexahydro-1,3a,8-trimethylpyrrolo[2,3-b]indol-5-ol, benzoate;
(3aS-cis)-7-bromo-1,2,3,3a,8,8a-hexahydro-1,3a,8-trimethylpyrrolo[2,3-b]indol-5-ol, 3,5-bis(1,1-dimethylethyl)-4-hydroxybenzoate;
(3aS-cis)-1,2,3,3a,8,8a-hexahydro-1,3a,8-trimethylpyrrolo[2,3-b]indol-5-ol, cyclooctyl carbamate ester;
(3aS-cis)-1,2,3,3a,8,8a-hexahydro-1,3a,8-trimethylpyrrolo[2,3-b]indol-5-ol, (cyclooctyl)methyl carbamate ester;
(3aS-cis)-1,2,3,3a,8,8a-hexahydro-1,3a,8-trimethylpyrrolo[2,3-b]indol-5-ol, [(S*)-(1-(4-bromophenyl)ethyl]-carbamate ester;
(3aS-cis)-1,2,3,3a,8,8a-hexahydro-1,3a,8-trimethylpyrrolo[2,3-b]indol-5-ol, [(S*)-(1-phenyl)ethyl]methyl carbamate ester;
(3aS-cis)-1,2,3,3a,8,8a-hexahydro-1,3a,8-trimethylpyrrolo[2,3-b]indol-5-ol, [(R*)-(1-phenyl)ethyl]methyl carbamate ester;
(3aS-cis)-1,2,3,3a,8,8a-hexahydro-1,3a,8-trimethylpyrrolo[2,3-b]indol-5-ol, (2-phenyl)propyl carbamate ester;
(3aS-cis)-1,2,3,3a,8,8a-hexahydro-1,3a,8-trimethylpyrrolo[2,3-b]indol-5-ol, (−)-cis-myrtanyl carbamate ester;
(3aS-cis)-1,2,3,3a,8,8a-hexahydro-5-(methoxymethoxy)-1,3a,8-trimethylpyrrolo[2,3-b]indole;
(3aS-cis)-7-bromo-1,2,3,3a, 8,8a-hexahydro-5-triisopropylsilyloxy-1,3a,8-trimethylpyrrolo[2,3-b]indole;
(3aS-cis)-1,2,3,3a,8,8a-hexahydro-1,3a,7,8a-tetramethyl-5-triisopropylsilyloxypyrrolo[2,3-b]indole;
(3aS-cis)-7-formyl-1,2,3,3a,8,8a-hexahydro-5-triisopropylsilyloxy-1,3a,8-trimethylpyrrolo[2,3-b]indole;
(3aS-cis)-7-formyl-1,2,3,3a,8,8a-hexahydro-1,3a,8-trimethylpyrrolo[2,3-b]indol-5-ol;
(3aS-cis)-7-formyl-1,2,3,3a,8,8a-hexahydro-1,3a,8-trimethylpyrrolo[2,3-b]indol-5-ol, methyl carbamate ester;
(3aS-cis)-6-formyl-1,2,3,3a,8,8a-hexahydro-1,3a,8-trimethylpyrrolo[2,3-b]indol-5-ol, N,N-diethyl carbamate ester;
(3aS-cis)-6-formyl-1,2,3,3a,8,8a-hexahydro-1,3a,8-trimethylpyrrolo[2,3-b]indol-5-ol;
(3aS-cis)-1,2,3,3a,8,8a-hexahydro-7-methylaminocarbonyl-5-triisopropylsilyloxy-1,3a,8-trimethylpyrrolo[2,3-b]indole;
(3aS-cis)-1,2,3,3a,8,8a-hexahydro-7-methylaminocarbonyl-1,3a,8-trimethylpyrrolo[2,3-b]indol-5-ol;
(3aS-cis)-1,2,3,3a,8,8a-hexahydro-1,3a,8-trimethylpyrrolo[2,3-b]indol-5-ol, cyclododecyl carbamate ester;
(3aS-cis)-1,2,3,3a,8,8a-hexahydro-1,3a,8-trimethylpyrrolo[2,3-b]indol-5-ol, (2,3-dihydro-1H-inden-1-yl) carbamate eser;
(3aS-cis)-1,2,3,3a,8,8a-hexahydro-1,3a,8-trimethylpyrrolo[2,3-b]indol-5-ol, 1-(1,2,3,4-tetrahydro)naphthyl carbamate ester;
(3aS-cis)-1,2,3,3a,8,8a-hexahydro-1,3a,8-trimethylpyrrolo[2,3-b]indol-5-ol, [(R*)-1-(1-naphthyl)ethyl] carbamate ester;
(3aS-cis)-1,2,3,3a,8,8a-hexahydro-1,3a,8-trimethylpyrrolo[2,3-b]indol-5-ol, (1-adamantyl)methyl carbamate ester; hexahydro-(1H)-azepine carboxylic acid, (3aS-cis)-1,2,3,3a,8,8a-hexahydro-1,3a,8-trimethylpyrrolo[2,3-b]indol-5-yl ester;
octahydroazocine carboxylic acid, (3aS-cis)-1,2,3,3a,8,,8a-hexahydro-1,3a,8-trimethylpyrrolo[2,3-b]indol-5-yl ester;
(3aS-cis)-1,2,3,3a,8,8a-hexahydro-1,3a,8-trimethylpyrrolo[2,3-b]indol-5-ol, (1,2,3,4-tetrahydroisoquinolinyl) carbamate ester;
(3aS-cis)-1,2,3,3a,8,8a-hexahydro-1,3a,8-trimethylpyrrolo[2,3-b]indol-5-ol, (1-methyl-1,2,3,4-tetrahydroisoquinolinyl) carbamate ester;
(3aS-cis)-1,2,3,3a,8,8a-hexahydro-1,3a,8-trimethylpyrrolo[2,3-b]indol-5-yl, [3-[3-azabicyclo[3.2.2]nonyl]]carbamate ester fumarate;
(3aS-cis)-1,2,3,3a,8,8a-hexahydro-5-(methoxymethoxy)-1,3a,8-trimethyl-6-(trimethylsilyl)pyrrolo[2,3-b]indole;

The present invention will be described below in further detail with reference to the following examples.

EXAMPLE 1

(3aS-cis)-1,2,3,3a,8,8a-Hexahydro-1,3a,8-trimethylpyrrolo[2,3-b]indol-5-ol, octadecyl carbamate ester A degassed solution containing octadecyl isocyanate (2.9 g) and eseroline (1.8 g) in 50 ml of dry tetrahydrofuran was treated with a catalytic chip of freshly cut sodium metal and thereafter stirred under a nitrogen blanket for 72 hours. The solution was then heated to reflux for 2 hours and thereafter evaporated. The residue was purified by flash chromatography (silica gel, 100:1 ethyl acetate/ethanol) to give 3.8 g of a wax. Recrystallization from ether gave 3.5 g of a white powder, mp 49°–50°. ANALYSIS: Calculated for $C_{32}H_{55}N_3O_2$: 74.80% C; 10.79% H; 8.17% N. Found: 74.57% C; 10.39% H; 8.00% N.

EXAMPLE 2

(3aS-cis)-7-Chloro-1,2,3,3a,8,8a-hexahydro-1,3a,8-trimethylpyrrolo[2,3-b]indol-5-ol, methyl carbamate ester A degassed solution of eserine (5.0 g) in 60 ml of methanol and 2 drops of concentrated hydrochloric acid was treated with N-chlorosuccinimide (2.6 g) in one portion with stirring. After 4 hours the solution was evaporated and the residue was purified by flash chromatography (silica gel, 4:1 ethyl acetate/methanol) to an oil. This oil was crystallized from hot ether to give 4.1 g of crystals, mp 129°–130° C.

ANALYSIS: Calculated for $C_{15}H_{20}ClN_3O_2$: 58.15% C; 6.50% H; 13.56% N. Found: 58.18% C; 6.54% H; 13.59% N.

EXAMPLE 3

(3aS-cis)-7-Bromo-1,2,3,3a,8,8a-hexahydro-1,3a,8-trimethylpyrrolo[2,3-b]indol-5-ol, methyl carbamate ester A degassed solution of eserine (2.0 g) in 50 ml of methanol and 2 drops of 48% HBr was treated with N-bromosuccinimide (1.4 g) in one portion. After 1 hour at room temperature, the solution was evaporated and the residue was purified by flash chromatography (silica gel, 4:1 ethyl acetate/methanol) to give an oil. This oil was crystallized from hot ether to give 1.6 g of crystals, mp 121°–122° C.

ANALYSIS: Calculated for $C_{15}H_{20}BrN_3O_2$: 50.85% C; 5.69% H; 11.86% N. Found: 50.73% C; 5.68% H; 11.76% N.

EXAMPLE 4

(3aS-cis)-1,2,3a,8,8a-Hexahydro-1,3a,8-trimethylpyrrolo[2,3-b]indol-5-ol, N,N-diethyl carbamate ester A solution of eseroline (1.5 g) and diethylcarbamyl chloride (2.7 g) in 50 ml of dry dimethylformamide was degassed and thereafter treated with milled potassium carbonate (2.7 g). This slurry was stirred at room temperature for 5 hours and thereafter poured into 600 ml of water and extracted with 300 ml of ethyl acetate. The organic phase was washed with brine, dried over anhydrous magnesium sulfate, filtered and evaporated to a thick oil. This oil was purified by flash chromatography (silica gel, 9:1 ethyl acetate/methanol) to an oil, which was crystallized from petroleum ether to give 1.7 g of crystals, mp 74°–76° C.

ANALYSIS: Calculated for $C_{18}H_{27}N_3O_2$: 68.10% C; 8.57% H; 13.23% N. Found: 67.95% C; 8.61% H; 12.98% N.

EXAMPLE 5

(3aS-cis)-1,2,3,3a,8,8a-Hexahydro-1,3a,8-trimethylpyrrolo[2,3-b]indol-5-ol, cyclopentylmethyl carbamate ester A degassed solution of eseroline (1.5 g) and cyclopentylmethyl isocyanate (1.2 g) in 70 ml of dry tetrahydrofuran was treated with a catalytic chip of sodium metal and heated under reflux for 3 hours. The solution was evaporated and the residue was purified by flash chromatography (silica gel, 4:1 ethyl acetate/methanol) to give a powder. This material was recrystallized from ether/petroleum ether to give 1.5 g of cubes, mp 105°–107° C.

ANALYSIS: Calculated for $C_{20}H_{29}N_3O_2$: 69.93% C; 8.51% H; 12.23% N. Found: 70.17% C; 8.70% H; 12.30% N.

EXAMPLE 6

(3aS-cis)-1,2,3,3a,8,8a-Hexahydro-1,3a,8-trimethylpyrrolo[2,3-b]indol-5-ol, (thien-3-yl)methyl carbamate ester A degassed solution containing eseroline (1.5 g) and (thien-3-yl)methyl isocyanate (1.5 g) in 60 ml of dry tetrahydrofuran was treated with a catalytic chip of sodium metal and thereafter stirred at 60° for 6 hours. The solution was evaporated and the residue was purified by high performance liquid chromatography (HPLC) (silica gel, 16:3 ethyl acetate/methanol) to give 1.5 g of an oil. This oil slowly crystallized from ether to give 1.3 g of crystals.

ANALYSIS: Calculated for $C_{19}H_{23}N_3O_2S$: 63.85% C; 6.48% H; 11.75% N. Found: 63.54% C; 6.61% H; 11.75% N.

EXAMPLE 7

(3aS-cis)-1,2,3,3a,8,8a-Hexahydro-1,3a,8-trimethylpyrrolo[2,3-b]indol-5-ol, benzyl carbamate ester A solution of eseroline (1.7 g) and benzyl isocyanate (1.2 g) in 70 ml of degassed tetrahydrofuran was treated with a catalytic chip of sodium metal and stirred at room temperature for ten hours. The volatiles were removed and the residue was recrystallized from acetone/petroleum ether to give 2.1 of a powder, mp 167°–169° C.

ANALYSIS: Calculated for $C_{21}H_{25}N_3O_2$: 71.76% C; 7.17% H; 11.95% N. Found: 71.55% C; 6.97% H; 11.95% N.

EXAMPLE 8

(3aS-cis)-1,2,3,3a,8,8a-Hexahydro-1,3a,8-trimethylpyrrolo[2,3-b]indol-5-ol, (2-phenyl)ethyl carbamate ester A solution of eseroline (1.3 g) and phenylethyl isocyanate (1.03 g) in 50 ml of degassed tetrahydrofuran was treated with a catalytic chip of sodium metal. The solution was heated to reflux for four hours and thereafter evaporated. The residue was recrystallized from acetone/petroleum ether to give 1.7 g of needles, mp 152°–155° C.

ANALYSIS: Calculated for $C_{22}H_{27}N_3O_2$: 72.29% C; 7.45% H; 11.49% N. Found: 72.33% C; 7.49% H; 11.56% N.

EXAMPLE 9

(3aS-cis)-1,2,3,3a,8,8a-Hexahydro-1,3a,8-trimethylpyrrolo[2,3-b]indol-5-ol, [(S*)-(1-phenyl)ethyl] carbamate ester A degassed solution containing eseroline (1.7 g) and S-(−)-α-methylbenzyl isocyanate (1.0 g) in 50 ml of dry tetrahydrofuran was treated with a catalytic chip of sodium metal and stirred at room temperature for one hour. This solution was heated under reflux for five hours and evaporated to a foam. This forma was purified by flash chromatography (alumina, ethyl acetate) and thereafter recrystallized from ether/petroleum ether to give 1.6 g of a powder, mp 113°–114° C.

ANALYSIS: Calculated for $C_{22}H_{27}N_3O_2$: 72.29% C; 7.45% H; 11.49% M. Found: 72.37% C; 7.68% H; 11.37% N.

EXAMPLE 10

(3aS-cis)-1,2,3,3a,8,8a-Hexahydro-1,3a,8-trimethylpyrrolo[2,3-b]indol-5-ol, [(R*)-(1-phenyl)ethyl] carbamate ester A degassed solution containing eseroline (1.5 g) and R-(+)-α-methylbenzyl isocyanate (1.0 g) in 60 ml of dry tetrahydrofuran was treated with a catalytic chip of sodium metal and stirred at room temperature for one hour. This solution was heated to reflux for five hours and thereafter evaporated. The residue was purified by flash chromatography (alumina, ethyl acetate) to a powder. This powder was recrystallized from ether/petroleum ether to give 2.0 g of crystals, mp 151°–153° C.

ANALYSIS: Calculated for $C_{22}H_{27}N_3O_2$: 72.29% C; 7.45% H; 11.49% N. Found: 72.10% C; 7.63% H; 11.36% N.

EXAMPLE 11

(3aS-cis)-7-Chloro-1,2,3,3a,8,8a-hexahydro-1,3a,8-trimethylpyrrolo[2,3-b]indol-5-ol, [(S*)-(1-phenyl)ethyl] carbamate ester A degassed solution containing 7-chloroeseroline (1.3 g) and S-(−)-α-methylbenzyl isocyanate (1.0 g) in 60 ml of dry tetrahydrofuran was treated with a catalytic chip of sodium metal and stirred at 50° for three hours. This solution was evaporated and the residue recrystallized twice from dichloromethane to give 1.4 g of crystals, mp 172°–173° C.

ANALYSIS: Calculated for $C_{22}H_{26}ClN_3O_2$: 66.07% C; 6.55% H; 10.50% N. Found: 65.81% C; 6.59% H; 10.43% N.

EXAMPLE 12

(3aS-cis)-7-Bromo-1,2,3,3a,8,8a-hexahydro-1,3a,8-trimethylpyrrolo[2,3-b]indol-5-ol, [(S*)-(1-phenyl)ethyl] carbamate ester A degassed solution of 7-bromoeseroline (1.5 g) and (S)-(−)-α-methylbenzyl isocyanate (1.0 g) in 60 ml of dry tetrahydrofuran was treated with a catalytic chip of sodium metal and stirred at 60° for four hours. The resulting solution was evaporated and the remaining powder recrystallized twice from chloroform to give 1.4 g of crystals, mp 183°–185° C.

ANALYSIS: Calculated for $C_{22}H_{26}BrN_3O_2$: 59.46% C; 5.89% H; 9.45% N. Found: 59.10% C; 5.80% H; 9.33% N.

EXAMPLE 13

(3aS-cis)-1,2,3,3a,8,8a-Hexahydro-1,3a,8-trimethylpyrrolo[2,3-b]indol-5-ol, [1-(1-naphthyl)ethyl]carbamate ester A solution containing eseroline (1.5 g) and racemic 1-(1-naphthyl) ethyl isocyanate (1.9 g) in 70 ml of dry tetrahydrofuran was degassed and treated with a catalytic chip of sodium metal. After 16 hours under reflux, the solution was evaporated and the residue was purified by flash chromatography (silica gel, 9:1 ethyl acetate/methanol) to give 1.9 g of a solid. This material was recrystallized from ether/petroleum ether to give 1.7 g of cubes, mp 147°–150° C.

ANALYSIS: Calculated for $C_{26}H_{29}N_3O_2$: 75.15% C; 7.03% H; 10.11% N. Found: 75.15% C; 7.09% H; 10.04% N.

EXAMPLE 14

(3aS-cis)-1,2,3,3a,8,8a-Hexahydro-1,3a,8-trimethylpyrrolo[2,3-b]indol-5-ol, cyclohexyl carbamate ester A degassed solution containing eseroline (1.5 g) and cyclohexyl isocyanate (1.2 g) in 70 ml of dry tetrahydrofuran was treated with a catalytic chip of sodium metal and stirred at ambient temperature. After 16 hours, the solution was heated to reflux for 1 hour and thereafter evaporated. The residue was purified by flash chromatography (silica gel, 16:1 ethyl acetate/ethanol) to give 2.0 g of an oil. This oil slowly crystallized from petroleum ether to give 1.3 g of a powder, mp 93°–95° C.

ANALYSIS: Calculated for $C_{20}H_{29}N_3O_2$: 69.93% C; 8.51% H; 12.23% N. Found: 69.66% C; 8.22% H; 12.05% N.

EXAMPLE 15

(3aS-cis)-7-Chloro-1,2,3,3a,8,8a-hexahydro-1,3a,8-trimethylpyrrolo[2,3-b]indol-5-ol, cyclohexyl carbamate ester A degassed solution containing 7-chloroeseroline (1.5 g) and cyclohexyl isocyanate (1.5 g) in 50 ml of dry tetrahydrofuran was treated with a catalytic chip of sodium metal and stirred at room temperature overnight. This solution was evaporated and the residue purified by column chromatography (neutral alumina, 9:1 ethyl acetate/dichloromethane) to give an oil. This oil was crystallized from ether to give 1.2 g of crystals, mp 154°–156°.

ANALYSIS: Calculated for $C_{20}H_{28}ClN_3O_2$: 63.56% C; 7.46% H; 11.12% N. Found: 63.38% C; 7.60% H; 10.83% N.

EXAMPLE 16

(3aS-cis)-7-Bromo-1,2,3,3a,8,8a-hexahydro-1,3a,8-trimethylpyrrolo[2,3-b]indol-5-ol, cyclohexyl carbamate ester A degassed solution containing 7-bromoeseroline (1.5 g) and cyclohexyl isocyanate (1.5 g) in 60 ml of dry tetrahydrofuran was treated with a catalytic chip of sodium metal and stirred at 50° for 3 hours. This solution was evaporated and the residue purified by column chromatography (alumina, 5:1 ethyl acetate/dichloromethane) to give 2.1 g of powder. This powder was crystallized from ether/petroleum ether to give 1.9 g of crystals, mp 163°–164°.

ANALYSIS: Calculated for $C_{20}H_{28}BrN_3O_2$: 56.68% C; 6.68% H; 9.95% N. Found: 56.98% C; 6.60% H; 9.88% N.

EXAMPLE 17

(3aS-cis)-1,2,3,3a,8,8a-Hexahydro-1,3a,8-trimethylpyrrolo[2,3-b]indol-5-ol, 4,4-dimethylcyclohexyl carbamate ester A degassed solution containing eseroline (1.5 g) and 4,4-dimethylcyclohexyl isocyanate (1.5 g) in 60 ml of dry tetrahydrofuran was treated with a catalytic chip of sodium metal, and thereafter stirred at 50° for 4 hours. The solution was evaporated and the residue purified by flash chromatography (silica gel, 9:1 ethyl acetate/methanol) to a foam. This foam crystallized from ether/petroleum ether to give 1.1 g of cubes, mp 98°–99° C.

ANALYSIS: Calculated for $C_{22}H_{33}N_3O_2$: 71.12% C; 8.95% H; 11.31% N. Found: 71.02% C; 9.04% H; 11.25% N.

EXAMPLE 18

(3aS-cis)-1,2,3,3a,8,8a-Hexahydro-1,3a,8-trimethylpyrrolo[2,3-b]indol-5-ol, 4-ethylcyclohexyl carbamate ester A degassed solution of eseroline (1.5 g) and 4-ethylcyclohexyl isocyanate (1.5 g) in 70 ml of dry tetrahydrofuran was treated with a catalytic chip of sodium metal and thereafter stirred under reflux for 4 hours. This solution was evaporated and the residue purified by flash chromatography (silica gel, 8:3 ethyl acetate/methanol) to give a powder. This powder was recrystallized from ether to give 1.3 g of crystals, mp 116°–118° C.

ANALYSIS: Calculated for $C_{22}H_{33}N_3O_2$: 71.12% C; 8.95% H; 11.31% N. Found: 70.82% C; 8.95H; 11.18% N.

EXAMPLE 19

(3aS-cis)-1,2,3,3a,8,8a-Hexahydro-1,3a,8-trimethylpyrrolo[2,3-b]indol-5-ol, spiro[5.5]undecan-3-yl carbamate ester A degassed solution containing eseroline (1.5 g) and spiro [5.5] undecan-3-yl-isocyanate (1.9 g) in 60 ml of dry tetrahydrofuran was treated with a catalytic chip of sodium metal. After 4 hours at 65° the solution was evaporated and the residue purified by flash chromatography (silica gel, 9:1 ethyl acetate/methanol). The residue was recrystallized from ether/petroleium ether to give 1.6 g of flakes, mp 110°–112° C.

ANALYSIS: Calculated for $C_{25}H_{37}N_3O_2$: 72.95% C; 9.06% H; 10.21% N. Found: 72.80% C; 8.84% H; 10.21% N.

EXAMPLE 20

(3aS-cis)-1,2,3,3a,8,8a-Hexahydro-1,3a,8-trimethylpyrrolo[2,3-b]indol-5-ol, cycloheptyl carbamate ester A degassed solution containing eseroline (1.5 g) and cycloheptyl isocyanate (1.39 g) in 50 ml of dry tetrahydrofuran was treated with a catalytic chip of sodium metal and thereafter stirred under reflux overnight. After 16 hours the solution was evaporated and the residue purified by flash chromatography (alumina, ethyl acetate) to an oil. This oil was crystallized from 1:1 ether/petroleum ether to give 1.6 g of crystals, mp 86°–88° C.

ANALYSIS: Calculated for $C_{21}H_{31}N_3O_2$: 70.55% C; 8.74% H; 11.75% N. Found: 70.62% C; 8.77% H; 11.66% N.

EXAMPLE 21

(3aS-cis)-1,2,3,3a,8,8a-Hexahydro-1,3a,8-trimethylpyrrolo[2,3-b]indol-5-ol, 1,2-dimethylcyclohexen-4-yl carbamate ester A degassed solution containing eseroline (1.5 g) and 1,2-dimethylcyclohexen-4-yl isocyanate (1.5 g) in 60 ml of dry tetrahydrofuran was treated with a catalytic chip of sodium metal, and stirred at room temperature overnight. The solution was evaporated and the residue purified by flash chromatography (silica gel, 9:1 ethyl acetate/methanol) to give a foam. This foam was crystallized from ether/petroleum ether to give 1.2 g of crystals, mp 134°–136° C.

ANALYSIS: Calculated for $C_{22}H_{31}N_3O_2$: 71.51% C; 8.45% H; 11.37% N. Found: 71.21% C; 8.51% H; 11.32% N.

EXAMPLE 22

(3aS-cis)-1,2,3,3a,8,8a-Hexahydro-1,3a,8-trimethylpyrrolo[2,3-b]indol-5-ol, cyclohexen-1-yl carbamate ester A degassed solution containing eseroline (1.5 g) and cyclohexen-1-yl isocyanate (1.5 g) in 70 ml of dry tetrahydrofuran was treated with a catalytic chip of sodium metal and stirred under reflux for 6 hours. The solution was evaporated and the residue purified by flash chromatography (silica gel, 9:1 ethyl acetate/methanol) to give 1.7 g of a powder. This material was recrystallized twice from ether/petroleum ether to give 1.5 g of crystals, mp 133°–134° C.

ANALYSIS: Calculated for $C_{20}H_{27}N_3O_2$: 70.35% C; 7.97% H; 12.30% N. Found: 70.20% C; 8.06% H; 12.25% N.

EXAMPLE 23

(3aS-cis)-1,2,3,3a,8,8a-Hexahydro-1,3a,8-trimethylpyrrolo[2,3-b]indol-5-ol, bicyclo[2.2.1]heptan-2-yl carbamate ester A degassed solution of eseroline (1.5 g) and bicyclo [2.2.1] heptan-2-yl-isocyanate (1.4 g) in 100 ml of dry tetrahydrofuran was treated with a catalytic chip of sodium metal and thereafter stirred under reflux with a nitrogen blanket overnight. The solution was evaporated and the residue purified by flash chromatography (silica gel, 9:1 ethyl acetate/methanol) to give 1.6 g of a foam which did not crystallize. This foam was heated to 55° at 0.1 mmHg for 5 hours. The resulting melt was pulverized to give 1.6 g of a powder.

ANALYSIS: Calculated for $C_{21}H_{29}N_3O_2$: 70.95% C; 8.22% H; 11.82% N. Found: 70.62% C; 8.29% H; 11.62% N.

EXAMPLE 24

(3aS-cis)-1,2,3,3a,8,8a-Hexahydro-1,3a,8-trimethylpyrrolo[2,3-b]indol-5-ol, 3-chlorophenyl carbamate ester A degassed solution containing eseroline (1.5 g) and 3-chlorophenyl isocyanate (1.5 g) in 70 ml of tetrahydrofuran was treated with a catalytic chip of sodium metal and thereafter stirred under reflux for 4 hours. The solution was evaporated and the residue purified by flash chromatography (silica gel, 9:1 ethyl acetate/methanol) to give an oil. This oil was crystallized from ether/petroleum ether to give 1.2 g of crystals, mp 99°–101° C.

ANALYSIS: Calculated for $C_{20}H_{22}ClN_3O_2$: 64.59% C; 5.96% H; 11.30% N. Found: 64.52% C; 5.93% H; 11.24% N.

EXAMPLE 25

(3aS-cis)-1,2,3,3a,8,8a-Hexahydro-1,3a,8-trimethylpyrrolo[2,3-b]indol-5-ol, 4-chlorophenyl carbamate ester A degassed solution of eseroline (1.5 g) and p-chlorophenyl isocyanate (1.5 g) in 70 ml of dry tetrahydrofuran was treated with a catalytic chip of sodium metal and thereafter stirred under reflux for 16 hours. The solution was evaporated and the residue recrystallized from ether to give 1.3 g of a powder, mp 188°–190° C.

ANALYSIS: Calculated for $C_{20}H_{22}ClN_3O_2$: 64.59% C; 5.96% H; 11.30% N. Found: 64.68% C; 6.32% H; 11.29% N.

EXAMPLE 26

(3aS-cis)-1,2,3,3a,8,8a-Hexahydro-1,3a,8-trimethylpyrrolo[2,3-b]indol-5-ol, 2,6-dimethylphenyl carbamate ester A degassed solution of eseroline (1.5 g) and 2,6-dimethylphenyl isocyanate (1.47 g) in 50 ml of dry tetrahydrofuran was treated with a catalytic chip of sodium metal and thereafter stirred under reflux for 16 hours. This solution was evaporated and the residue purified by flash chromatography (alumina, ethyl acetate). The resulting solid was recrystallized from ether/petroleum ether to give 1.3 g of crystals, mp 80°–82° C.

ANALYSIS: Calculated for $C_{22}H_{27}N_3O_2$: 72.29% C; 7.44% H; 11.49% N. Found: 72.07% C; 7.75% H; 11.10% N.

EXAMPLE 27

(3aS-cis)-1,2,3,3a,8,8a-Hexahydro-1,3a,8-trimethylpyrrolo -[2,3-b]indol-5-ol, 4-nitrophenyl carbamate ester A mixture of eseroline (1.5 g) and 4-nitrophenyl isocyanate (1.6 g) in 70 ml of dry tetrahydrofuran was degassed and treated with a catalytic chip of sodium metal. The mixture was stirred under reflux for 4 hours and thereafter evaporated to a powder. This powder was purified by flash chromatography (silica gel, 19:1 dichloromethane/methanol) and the residue was triturated in ether to give 1.3 g of a powder, mp 199°–201° C.

ANALYSIS: Calculated for $C_{20}H_{22}N_4O_4$: 62.81% C; 5.80% H; 14.65% N. Found: 62.61% C; 5.87% H; 14.70% N.

EXAMPLE 28

(3aS-cis)-1,2,3,3a,8,8a-Hexahydro-1,3a,8-trimethylpyrrolo[2,3-b]indol-5-ol, 4-pyridinyl carbamate ester A mixture of eseroline (1.5 g) and 4-pyridyl isocyanate (1.4 g) in 70 ml of dry tetrahydrofuran was degassed and treated with a catalytic chip of sodium metal. This slurry was heated under reflux with a nitrogen blanket for 16 hours. The resulting solution was evaporated and the residue taken in an aqueous maleic acid solution. This solution was washed with two 100 ml portions of ethyl acetate and the layers were separated. The free base was liberated with saturated sodium bicarbonate and extracted into 200 ml of ethyl acetate. The residue upon evaporation was purified by flash chromatography (silica gel, 4:1, ethyl acetate/methanol) and the concentrated fractions were treated with 100 ml of ether. Upon cooling, 1.2 g of a powder precipitated, mp 163°–165° C.

ANALYSIS: Calculated for $C_{19}H_{22}N_4O_2$: 67.43% C; 6.55% H; 16.55% N. Found: 67.08% C; 6.75% H; 15.83% N.

EXAMPLE 29

(3aS-cis)-1,2,3,3a,8,8a-Hexahydro-1,3a,8-trimethylpyrrolo-[2,3-b]indol-5-ol, 4-methyl-1-piperazinyl carbamate ester A degassed solution of eseroline (1.5 g) in 35 ml of dichloromethane was treated in one portion with 1,1'-carbonyldiimidazole (2.2 g) and stirred at room temperature for 1 hour. This solution was then treated with N-methylpiperazine (3.0 g) and stirred at room temperature for 4 additional hours and thereafter evaporated to an oil. This oil was purified by column chromatography (neutral alumina, 4:1 dichloromethane/ethyl acetate) to give 1.9 g of an oil. This oil crystallized from cold petroleum ether to give 1.6 g of crystals, mp 69°–71° C.

ANALYSIS: Calculated for $C_{19}H_{20}N_4O_2$: 66.25% C; 8.19% H; 16.26% N. Found: 65.94% C; 8.17% H; 16.23% N.

EXAMPLE 30

(3aS-cis)-1,2,3,3a,8,8a-Hexahydro-1,3a,8-trimethylpyrrolo[2,3-b]indol-5-ol, 4-morpholinyl carbamate ester A degassed solution of eseroline (1.7 g) in 30 ml of dichloromethane was treated in one portion with 1,1'-carbonyl diimidazole (1.4 g) and stirred at room temperature for 1 hour. This solution was evaporated and the intermediate carbamate was taken up in 60 ml of dry ether and treated with morpholine (5.0 g). After 4 hours of reflux, this solution was evaporated and the residue purified by HPLC (silica gel, 8:1 ethyl acetate/methanol) to give 2.1 g of an oil. This oil was crystallized twice from ether to give 1.6 g of crystals, mp 108°–110°.

ANALYSIS: Calculated for $C_{18}H_{25}N_3O_3$: 65.23% C; 7.60% H; 12.68% N. Found: 65.31% C; 7.70% H; 12.72% N.

EXAMPLE 31

(3aS-cis)-1,2,3,3a,8,8a-Hexahydro-1,3a,8-trimethylpyrrolo[2,3-b]indol-5-ol, 4-morpholinyl thiocarbamate ester A degassed solution of eseroline (2.5 g) in 50 ml of dichloromethane was treated with 1,1'-thiocarbonyldiimidazole (3.1 g) in three portions over 5 minutes with stirring. After 45 minutes, this solution was treated with morpholine (4.4 g) and stirred at room temperature for 2 hours. This solution was evaporated and the residue purified by column chromatography (neutral alumina, 9:1 dichloromethane/ethyl acetate) to give 2.8 g of an oil. This oil crystallized from ether to give 2.6 g of crystals, mp 128°–130° C.

ANALYSIS: Calculated for $C_{18}H_{25}N_3O_2S$: 62.22% C; 7.25% H; 12.09% N. Found: 62.18% C; 7.42% H; 12.05% N.

EXAMPLE 32

(3aS-cis)-1,2,3,3a,8,8a-Hexahydro-1,3a,8-trimethylpyrrolo[2,3-b]indol-5-ol, 2-(2,6-dichlorophenylimino)-1-imidazolidinyl carbamate ester A solution of eseroline (2.5 g) in 60 ml of dichloromethane was treated with solid 1,1'-carbonyldiimidazole (2.7 g) in one portion and stirred at room temperature for 45 minutes. This solution was treated with solid 2-(2,6-dichlorophenylimino)imidazolidine (4.0 g) in two portions over 2 minutes and stirred at room temperature for 6 hours. This solution was evaporated and the residue purified by column chromatography (neutral alumina, 1:1 ethyl acetate/dichloromethane) to give 4 g of crystals. This material was triturated with ether to give 3.7 g of crystals, mp 165°–167°.

ANALYSIS: Calculated for $C_{23}H_{25}Cl_2N_5O_2$: 58.22% C; 5.31% H; 14.76% N. Found: 58.17% C; 5.39% H; 14.59% N.

EXAMPLE 33

(3aS-cis)-7-Chloro-1,2,3,3a,8,8a-hexahydro-1,3a,8-trimethylpyrrolo[2,3-b]indol-5-ol, (7-Chloroeseroline)

A mixture prepared from 2.4 g of 7-chloro-(3aS-cis)-1,2,3,3a,8,8a-hexahydro-1,3a,8-trimethylpyrrolo[2,3-b]indol-5-ol, methyl carbamate ester in 5 ml of ethanol and 1.0 g of sodium hydroxide in 10 ml of water was degassed and stirred at 40° for 4 hours. The resulting solution was quenched with 100 ml of saturated sodium bicarbonate solution and thereafter extracted with ethyl acetate (2×100 ml). The combined extracts were dried over anhydrous magnesium sulfate, filtered and evaporated to give 1.7 g of powder. An analytical sample was prepared by sublimation (0.1 mmHg, 145°) of the powder to give crystals, mp 152°–154°.

ANALYSIS: Calculated for $C_{13}N_{17}ClN_2O$: 61.77% C; 6.78% H; 11.08% N. Found: 61.73% C; 6.74% H; 11.02% N.

EXAMPLE 34

(3aS-cis)-7-Bromo-1,2,3,3a,8,8a-hexahydro-1,3a,8-trimethylpyrrolo[2,3-b]indol-5-ol, (7-Bromoeseroline)

A mixture prepared from 5.1 g of 7-bromo-(3aS-cis)-1,2,3,3a,8,8a-hexahydro-1,3a,8-trimethylpyrrolo[2,3-b]indol-5-ol, methyl carbamate ester in 5 ml of ethanol and 2.0 g of sodium hydroxide in 20 ml of water was degassed and stirred at room temperature for 6 hours. The resulting solution was quenched with 200 ml of saturated sodium bicarbonate solution and thereafter extracted with ethyl acetate (3×100 ml). The combined extracts were dried over anhydrous magnesium sulfate, filtered and evaporated to give 4.1 g of powder. An analytical sample was prepared by sublimation (0.1 mmHg, 160°) of the powder to give crystals, mp 175°–177° C.

ANALYSIS: Calculated for $C_{13}H_{17}BrN_2O$: 52.53% C; 5.76% H; 9.42% N. Found: 52.46% C; 5.63% H; 9.44% N.

EXAMPLE 35

(3aS-cis)-7-Bromo-1,2,3,3a,8,8a-hexahydro-1,3a,8-trimethylpyrrolo[2,3-b]indol-5-ol, 3-chlorophenyl carbamate ester fumarate A degassed mixture of 2.50 g of 7-bromo-(3aS-cis)-1,2,3,3a,8,8a-hexahydro-1,3a,8-trimethylpyrrolo[2,3-b]indol-5-ol, 1.53 g of 3-chlorophenylisocyanate and 0.2 ml of triethylamine in 150 ml of dry benzene was stirred under nitrogen for 5 hours. The solvent was then evaporated in vacuo and the residue was dissolved in 50 ml of ether. To this was added a solution of 1.0 g of fumaric acid in methanol followed by petroleum ether to precipitate the product as the fumarate salt. This was recrystallized from a solvent mixture of methanol/ether/petroleum ether to afford 3.0 g of crystals, mp 170° C., dec.

ANALYSIS: Calculated for $C_{20}H_{21}BrClN_3O_2 \cdot C_4H_4O_4$: 50.85% C; 4.45% H; 7.41% N. Found: 50.68% C; 4.75% H; 7.48% N.

EXAMPLE 36

(3aS-cis)-1,2,3,3a,8,8a-Hexahydro-1,3a,8-trimethyl-7-nitropyrrolo[2,3-b]indol-5-ol, methyl carbamate ester A degassed solution of 5.00 g of (3aS-cis)-1,2,3,3a,8,8a-hexahydro-1,3a,8-trimethylpyrrolo[2,3-b]indol-5-ol, methyl carbamate ester in 250 ml of acetonitrile was cooled to −23° C. in a bath of carbon tetrachloride/dry ice. A solution of 3.32 g of nitronium tetrafluoroborate in 150 ml of degassed acetonitrile was added dropwise, with stirring, over a period of 10 minutes and the solution was stirred in the cold for an additional 20 minutes. The reaction liquid was then poured into 1.3 liters of dilute sodium bicarbonate/ice mixture. The product was extracted into ethyl acetate (500 ml, 2×300 ml). The combined extracts were washed twice with brine, dried over magnesium sulfate and concentrated to an oil. This was purified by flash chromatography over silica gel using 1% methanol in dichloromethane as eluent. The fractions containing the product were combined and concentrated to an oil which crystallized from a mixed solvent of ether/hexane to give 0.85 g of crystals, mp 108°–109° C.

ANALYSIS: Calculated for $C_{15}H_{20}N_4O_4$: 56.24% C; 6.29% H; 17.49% N. Found: 56.07% C; 6.47% H; 17.24% N.

EXAMPLE 37

(3aS-cis)-7-Acetylamino-1,2,3,3a,8,8a-hexahydro-1,3a,8-trimethylpyrrolo[2,3-b]indol-5-ol, methyl carbamate ester A Parr hydrogenation bottle is charged with 3.20 g of (3aS-cis)-1,2,3,3a,8,8a-hexahydro-7-nitro-1,3a,8-trimethylpyrrolo[2,3-b]indol-5-ol, methyl carbamate ester, 0.3 g of 1% platinum-on-carbon catalyst, 1.53 g of acetic anhydride and 50 ml of degassed tetrahydrofuran. The mixture is shaken at room temperature under an initial hydrogen pressure of 40 psi (pounds per square inch) until uptake of hydrogen ceases. The catalyst is removed by filtration and the filtrate is concentrated in vacuo to afford (3aS-cis)-7-acetylamino-1,2,3,3a,8,8a-hexahydro-1,3a,8-trimethylpyrrolo[2,3-b]indol-5-ol, methyl carbamate ester.

EXAMPLE 38

(3aS-cis)-7-Bromo-1,2,3,3a,8,8a-hexahydro-1,3a,8-trimethylpyrrolo[2,3-b]indol-5-ol, trimethylacetate hydrochloride A solution of 0.69 g of trimethylacetic acid and 1.10 g of 1,1'-carbonyldiimidazole in 100 ml of dry, degassed tetrahydrofuran was refluxed for 1 hour. The reaction mixture was cooled to room temperature, and 2.00 g of (3aS)-7-bromo-1,2,3,3a,8,8a-hexahydro-1,3a,8-trimethylpyrrolo[2,3-b]indol-5-ol was added. The reaction mixture was stirred overnight and then the solvent was removed in vacuo. The residue was triturated with dichloromethane/petroleum ether to precipitate the imidazole by-product. This was filtered, and the filtrate containing the desired product was concentrated to an oil. The oil was purified by chromatography over neutral alumina using dichloromethane as eluent. The fractions containing the purified product were combined and the solvent was removed to provide 2.1 g of viscous oil. This was dissolved in ether, and the solution was cooled in a dry ice/acetone bath and made acidic by addition of ethereal hydrogen chloride. Addition of petroleum ether caused the product to precipitate. Recrystallization twice from ether/ethanol furnished pure crystals of (3aS-cis)-7-bromo-1,2,3,3a,8,8a-hexahydro-1,3a,8-trimethylpyrrolo[2,3-b]indol-5-ol trimethylacetate hydrochloride, mp 214°–215° C.

ANALYSIS: Calculated for $C_{18}H_{26}BrN_2O_2 \cdot HCl$: 51.63% C; 6.50% H; 6.69% N. Found: 51.60% C; 6.26% H; 6.71% N.

EXAMPLE 39

(3aS-cis)-7-Bromo-1,2,3,3a,8,8a-hexahydro-1,3a,8-trimethylpyrrolo[2,3-b]indol-5-ol, diphenylacetate A stirred solution of 2.75 g of diphenylacetic acid and 2.10 g of 1,1'-carbonyldiimidazole in 150 ml of dry, degassed tetrahydrofuran was refluxed until evolution of carbon dioxide gas ceased. The reaction solution was cooled to room temperature and 3.50 g of 7-bromo-(3aS-cis)-1,2,3,3a, 8,8a-hexahydro-1,3a,8-trimethylpyrrolo[2,3-b]indol-5-ol was added under nitrogen. The reaction solution was stirred overnight and then the solvent was removed, leaving an oily residue. This was purified by chromatography over neutral alumina using dicholoromethane as eluent. The fractions containing the product were combined and concentrated to an oil which crystallized from hexane. This material was recrystallized three times from hexane to give 1.9 g of crystals of (3aS-cis)-7-bromo-1,2,3,3a,8,8a-hexahydro-1,3a,8-trimethylpyrrolo[2,3-b]indol-5-ol diphenylacetate, mp 93°–95° C.

ANALYSIS: Calculated for $C_{27}H_{27}BrN_2O_2$: 66.00% C; 5.54% H; 5.70% N. Found: 66.01% C; 5.68% H; 5.64% N.

EXAMPLE 40

(3aS-cis)-5-Ethoxy-1,2,3,3a,8,8a-hexahydro-1,3a,8-trimethyl-7-nitropyrrolo[2,3-b]indole A degassed solution, under nitrogen, of 3.70 g of (3aS-cis)-5-ethoxy-1,2,3,3a,8,8a-hexahydro-1,3a,8-trimethylpyrrolo[2,3-b]indole in 50 ml of dry chloroform was treated with 2.00 g of nitronium tetrafluoroborate at a reaction temperature of +10°. After twenty minutes, the reaction was quenched by the addition of ice and saturated sodium bicarbonate solution with vigorous stirring. The organic layer was separated, dried over anhydrous sodium sulfate and concentrated to an oil. This was purified by chromatography over silica gel using ethyl acetate as the eluent. The fractions containing the product were combined and concentrated to an oil which crystallized from hexane to afford crystals of pure (3aS-cis)-5-ethoxy-1,2,3,3a,8,8a-hexahydro-1,3a,8-trimethyl-7-nitropyrrol[2,3-b]indole, mp 106°–108° C.

ANALYSIS: Calculated for $C_{15}H_{21}N_3O_3$: 61.84% C; 7.27% H; 14.44% N. Found: 61.88% C; 7.26% H; 14.35% N.

EXAMPLE 41

(3aS-cis)-1,2,3,3a,8,8a-Hexahydro-1,3a,8-trimethyl-7-nitropyrrolo[2,3-b]indol-5-ol, (7-Nitroeseroline)

A stirred solution, under nitrogen, of 1.85 g of (3aS-cis)-1,2,3,3a,8,8a-hexahydro-1,3a,8-trimethyl-7-nitropyrrolo[2,3-b]indol-5-ol, methyl carbamate ester in 50 ml of degassed tetrahydrofuran was treated with 0.65 g of potassium t-butoxide. Thirty minutes thereafter the mixture was partitioned between 300 ml of 50% aqueous ammonium chloride solution and 300 ml of ethyl acetate. The aqueous phase was separated and back-extracted with two 150 ml portions of ethyl acetate. The organic phases were combined, washed with saturated aqueous sodium chloride solution, dried over anhydrous magnesium sulfate and concentrated to an oil. This material was purified by flash chromatography over 50 g of silica gel packed in 1% methanol in dichloromethane, and eluted first with the same solvent mixture (2 liters) and then with 1.5% methanol in dichloromethane (2 liters). The fractions containing the purified product were combined and concentrated in vacuo to 0.8 g of solid. This was recrystallized from ethanol-hexane to provide crystals of pure (3aS-cis)-1,2,3,3a8,8a-hexahydro-1,3a,8-trimethyl-7-nitropyrrolo[2,3-b]indo-5-ol, mp 170°–171° C. Both NMR and elemental analysis indicated that this compound had crystallized as a solvate with 0.25 mole of ethanol.

ANALYSIS: Calculated for $C_{13}H_{17}N_3O_3 \cdot 0.25 CH_3CH_2OH$: 59.00% C; 6.78% H; 15.29% N. Found: 58.98% C; 6.92% H; 15.29% N.

EXAMPLE 42

(3aS-cis)-1,2,3,3a,8,8a-Hexahydro-1,3a,8-trimethyl-7-nitropyrrolo[2,3-b]indol-5-ol acetate fumarate A stirred solution of 2.52 g of 7-nitroeseroline in 25 ml of degassed tetrahydrofuran was cooled under nitrogen to 0° C. and treated with 1.26 g of triethylamine followed by 1.03 g of acetic anhydride. After thirty minutes the solution was decanted into 400 ml of a mixture of ammonium chloride/sodium chloride/ice water. The product was extracted with ethyl acetate (3×200 ml). The combined organic extracts were washed with brine, dried over anhydrous magnesium sulfate, and then concentrated to an oil. This material was purified by flash chromatography over 55 g of silica gel packed in dichloromethane containing 1% diethylamine. Elution with dichloromethane (1.5 liters), followed by 0.5% methanol in dichloromethane (2 liters) brought forth fractions containing the pure product. These were combined and concentrated to 1.66 g of oil. This oil was dissolved in 10 ml of ethanol and then there was added a solution of 0.63 g of fumaric acid in 5 ml of ethanol. The product crystallized as the fumarate salt upon addition of about 15 ml of hexane. This provided 1.62 g of pure crystals, mp 122°–123° C.

ANALYSIS: Calculated for $C_{15}H_{19}N_3O_4 \cdot C_4H_4O_4$: 54.15% C; 5.50% H; 9.97% N. Found: 53.86% C; 5.48% H; 9.64% N.

EXAMPLE 43

(3aS-cis)-7-Bromo-1,2,3,3a,8,8a-hexahydro-1,3a,8-trimethylpyrrolo[2,3-b]indol-5-ol acetate hydrochloride A mixture of 3.0 g of 7-bromoeseroline and 86 mg of sodium bicarbonate in 30 ml of tetrahydrofuran was degassed and kept under $N_2$ at 0° C. Potassium t-butoxide (120 mg) was charged in one portion and the mixture was stirred for twenty minutes. Then 1.08 g of acetic anhydride was added dropwise. After thirty minutes of stirring, thin layer chromatography indicated the reaction was complete. The mixture was quenched with methanol (2 ml) and thereafter concentrated to a solid. This product was extracted into ether (50 ml) and the insolubles were filtered. Treatment with a solution of HCl (generated by acetyl chloride, 800 mg; MeOH, 4 ml; ether, 75 ml) with stirring at 0° C. resulted in crystallization of the hydrochloride salt (2.0 g), mp 218°–221° C. dec.

ANALYSIS: Calculated for $C_{15}H_{19}BrN_2O_2.HCL$: 47.95% C; 5.37% H; 7.46% N. Found: 47.66% C; 5.35% H; 7.57% N.

EXAMPLE 44

(3aS-cis)-7-Amino-1,2,3,3a,8,8a-hexahydro-1,3a,8-trimethylpyrrolo[2,3-b]indol-5-ol, methyl carbamate ester A Parr hydrogenation bottle was charged with 2.5 g of (3aS-cis)-1,2,3,3a,8,8a-hexahydro-1,3a,8-trimethyl-7-nitropyrrolo[2,3-b]indol-5-ol, methyl carbamate ester (from Example 36), 0.40 g of 1% platinum-on-carbon catalyst and 200 ml of methanol. The mixture was shaken under 55 psi (pounds per square inch) of hydrogen gas pressure until uptake of hydrogen ceased. The mixture was then filtered to remove the catalyst and the solvent was removed at reduced pressure. The residual oil was purified by chromatography over 20 g of silica gel using 1% methanol in dichloromethane as eluent, followed by 25% methanol in dichloromethane. The fractions containing the purified product were combined and concentrated to afford 1.25 g. This material was dissolved in a mixture of 3 ml of methanol and 7 ml of ether. Hexane was then added dropwise to the turbidity point, and then the mixture was stirred at −10° C. The pure crystals were collected and found to weigh 0.34 g with mp 151°–152.5° C.

ANALYSIS: Calculated for $C_{15}H_{22}N_4O_2$: 62.12% C; 7.64% H; 19.30% N. Found: 61.54% C; 7.74% H; 18.92% N.

EXAMPLE 45

7-Bromo-1,2,3,3a,8,8a-hexahydro-3a,8-dimethylpyrrolo[2,3-b]indol-5-ol salicylate A solution of boron tribromide (36 ml of 1.0M in dichloromethane, DCM) was stirred at −15° C. under nitrogen as a solution of d,1-7-bromonoresermethole (3.00 g) in 75 ml of dry DCM was added slowly dropwise. The resultant slurry was maintained between −15° C. and −10° C. for two hours and then quenched with the dropwise addition of 200 ml of degassed NaHCO₃ solution. The mixture was extracted with 4:1 chloroform/isopropanol and the combined organic extracts were dried ($Na_2SO_4$), filtered and concentrated. The residue was purified by column chromatography (alumina; 4–7% MeOH/DCM) to give 1.50 g of foam. The salicylate salt of this material was formed in an ether/ethanol mixture and more ether was added to induce crystallization. The precipitate was recrystallized from ethyl acetate to give 1.10 g of crystals, mp 195°–197° C. (dec).

ANALYSIS: Calculated for $C_{12}H_{15}BrN_2O.C_7H_6O_3$: 54.16% C; 5.03% H; 6.65% N. Found: 53.89% C; 5.00% H; 6.49% N.

EXAMPLE 46

7-Bromo-1,2,3,3a,8,8a-hexahydro-5-methoxy-1,3a,8-trimethylpyrrolo[2,3-b]indole hydrobromide A solution of d,1-esermethole (14.75 g) in 100 ml of dry chloroform was degassed and stirred at −15° C. under nitrogen as N-bromosuccinimide (13.56 g) was added in portions over one hour. The reaction mixture was stirred at −10° C. under nitrogen for five hours and then the chloroform was evaporated. The residue was purified by HPLC (silica gel; 2–5% MeOH/DCM) to give 11.0 g of oil. Two grams of this material was dissolved in ether and treated with ethereal HBr until acidic to wet Litmus paper. The precipitate was collected and recrystallized from ethanol/ether to give 1.9 g of white crystals, mp 206°–207° C. (dec).

ANALYSIS: Calculated for $C_{14}H_{19}BrN_2O.HBr$: 42.88% C; 5.14% H; 7.15% N. Found: 43.03% C; 5.12% H; 7.19% N.

EXAMPLE 47

7-Bromo-1,2,3,3a,8,8a-hexahydro-1,3a,8-trimethylpyrrolo[2,3-b]indol-5-ol

A 1.0M $BBr_3$ solution in dichloromethane (DCM, 45 ml) was stirred at −10° C. under nitrogen as d,1-7-bromoesermethole (4.00 g) from the previous Example dissolved in 40 ml of dry DCM was added dropwise. The resultant slurry was stirred at ambient temperature for two hours and then quenched by the dropwise addition of 100 ml of saturated NaHCO₃ solution. The mixture was diluted to 500 ml with NaHCO₃ solution and stirred 20 minutes. The pH was adjusted to about 9 with $K_2CO_3$ and extracted with 4:1 chloroform/isopropanol. The combined organic extracts were dried ($Na_2SO_4$), filtered and concentrated. The resulting solid was triturated with ether and then recrystallized from ethyl acetate to give 2.1 g of off-white crystals, mp 197°–199° C.

ANALYSIS: Calculated for $C_{13}H_{17}BrN_2O$: 52.53% C; 5.77% H; 9.43% N. Found: 52.58% C; 5.78% H; 9.40% N.

EXAMPLE 48

7-Bromo-1-ethyl-1,2,3,3a,8,8a-hexahydro-5-methoxy-3a,8-dimethylpyrrolo[2,3-b]indole hydrobromide A solution prepared from d,1-7-bromonoresermethole (5.00 g), diisopropylethylamine (6.52 g), bromoethane (4.04 g), and 75 ml of dry acetonitrile was stirred at 45° C. under nitrogen for seventy-two hours. The solvent was evaporated and the residue purified by flash chromatography (silica gel; 2–5% MeOH/DCM). This material was then purified again by flash chromatography (silica gel: EtOAc) and the resulting oil treated with ethereal HBr until acidic to wet Litmus paper. The precipitate was collected and recrystallized twice from ethanol/ether to give 2.3 g of crystals, mp 201°–202° C. (dec).

ANALYSIS: Calculated for $C_{15}H_{21}BrN_2O.HBr$: 44.35% C; 5.46% H; 6.90% N. Found: 44.43% C; 5.55% H; 6.80% N.

EXAMPLE 49

7-Bromo-1-ethyl-1,2,3,3a,8,8a-hexahydro-3a,8-dimethylpyrrolo[2,3-b]indol-5-ol salicylate A solution of boron tribromide (27 ml of 1.0M in dichloromethane, DCM) was stirred at −15° C. under nitrogen as a solution of 7-bromo-1-ethyl-1,2,3,3a,8,8a-hexahydro-5-methoxy-3a,8-dimethylpyrrolo[2,3-b]indole (2.50 g) in 75 ml of dry DCM was added dropwise. The reaction mixture was stirred under nitrogen overnight and thereafter allowed to warm to room temperature. The reaction was quenched with 100 ml of degassed $NaHCO_3$ solution added dropwise. An additional 400 ml of $NaHCO_3$ solution was added and the product was extracted with 4:1 chloroform/isopropanol. The combined organic extracts were dried ($Na_2SO_4$), filtered and concentrated. The residue was purified by column chromatography (alumina; 2–6% MeOH/DCM) and the salicylate salt was formed in ether with a littel ethanol added for solubility. After cooling, the precipitate was collected and recrystallized from ethanol/ethyl acetate to give 2.2 g of pure crystals, mp 208°–209° C. (dec).

ANALYSIS: Calculated for $C_{14}H_{19}BrN_2O.C_7H_6O_3$: 56.13% C; 5.61% H; 6.24% N. Found: 56.20% C; 5.60% H; 6.19% N.

EXAMPLE 50

7-Bromo-1,2,3,3a,8,8a-hexahydro-5-methoxy-3a,8-dimethyl-1-propylpyrrolo[2,3-b]indole hydrobromide A solution prepared from d,1-7-bromonoresermethole (6.00 g), diisopropylethylamine (7.83 g), 1-iodopropane (3.78 g) and 150 ml of acetonitrile was degassed and stirred at 60° C. under nitrogen overnight. The solvent was evaporated and the residue purified by flash chromotography (silica gel; 2–5% MeOH/DCM) to give 3.6 g of oil. This material was dissolved in ether and treated with ethereal HBr until acidic to wet Litmus paper. The precipitate was collected and recrystallized from ethanol/ether to give 3.3 g of white crystals, mp 207°–208° C. (dec).

ANALYSIS: Calculated for $C_{16}H_{23}BrN_2O.HBr$: 45.73% C; 5.76% H; 6.67% N. Found: 45.79% C; 5.78% H; 6.61% N.

EXAMPLE 51

7-Bromo-1,2,3,3a,8,8a-hexahydro-3a,8-dimethyl-1-propylpyrrolo[2,3-b]indol-5-ol salicylate A solution prepared from 21 ml of 1.0M boron tribromide solution in dichloromethane (DCM) and 20 ml of dry DCM was degassed and stirred at −15° C. under nitrogen as a solution of 7-bromo-1,2,3,3a,8,8a-hexahydro-5-methoxy-3a,8-dimethyl-1-propylpyrrolo[2,3-b]indole (2.00 g) in 60 ml of dry DCM was added dropwise. The resulting slurry was stirred at 0° C. under nitrogen for four hours and then quenched with 100 ml of $NaHCO_3$ solution added dropwise. An additional 300 ml of $NaHCO_3$ solution was added and the slurry extracted with 4:1 chloroform/isopropanol. The combined organic extracts were dried ($Na_2SO_4$), filtered and concentrated. The residue was purified by column chromatography (alumina; 2–6% MeOH/DCM) and the salicylate salt was formed in ether with a small amount of ethanol added for solubility. The addition of more ether and cooling resulted in precipitation of the salt which was collected and recrystallized from ethyl acetate to give 1.7 g of crystals, mp 193°–195° C. (dec).

ANALYSIS: Calculated for $C_{15}H_{21}BrN_2O.C_7H_6O_3$: 57.02% C; 5.87% H; 6.05% N. Found: 57.05% C; 5.84% H; 6.01% N.

EXAMPLE 52

1,2,3,3a,8,8a-Hexahydro-5-methoxy-3a,8-dimethyl-1-(2-propenyl)-pyrrolo[2,3-b]indole hydrochloride A solution prepared from d,1-esermethole (7.00 g), diisopropyl ethylamine (20.72 g), and 50 of dry acetonitrile was stirred at 0° C. under nitrogen as a solution of allyl bromide (4.27 g) in 40 ml of dry acetonitrile was added dropwise. The solution was stirred at ambient temperature for three hours and the solvent was evaporated. The residue was purified by HPLC (silica; 5% MeOH/DCM) and then distilled under vacuum in a Kugelrohr (oven temperature=140° C. @ 0.40 mm Hg) to give 6.7 g of opaque oil. 3 g of this material was dissolved in ether and treated with ethereal HCl until acidic to wet Litmus paper. The precipitate was collected and recrystallized from isopropanol/ether to give 2.9 g of white crystals, mp 164°–166° C.

ANALYSIS: Calculated for $C_{16}H_{22}N_2O.HCl$: 65.18% C; 7.86% H; 9.50% N. Found: 64.86% C; 7.74% H; 9.47% N.

EXAMPLE 53

1,2,3,3a,8,8a-Hexahydro-3a,8-dimethyl-1-(2-propenyl)-pyrrolo[2,3-b]indol-5-ol salicylate A 1.0M $BBr_3$ solution (52 ml) in dichloromethane was stirred at −5° C. under nitrogen as 1,2,3,3a,8,8a-hexahydro-5-methoxy-3a,8-dimethyl-1-(2-propenyl)-pyrrolo[2,3-b]indole (3.85 g) dissolved in 50 ml of dry dichloromethane was added dropwise. The mixture was stirred at 0° C. for one hour and then quenched by the dropwise addition of 35 ml of water. The mixture was basified with 300 ml of saturated $NaHCO_3$ solution and stirred 20 minutes to break up any boron complexes. A little $K_2CO_3$ was added until pH 9 was reached and the suspension was extracted with 4:1 chloroform/isopropanol. The combined organic extracts were dried ($Na_2SO_4$), filtered and concentrated. The salicylate of this material was formed in methanol/ether and crystallized out with the addition of more ether. The collected precipitate was recrystallized from ethyl acetate to give 4.0 g of crystals, mp 154°–155° C.

ANALYSIS: Calculated for $C_{15}H_{20}N_2O.C_7H_6O_3$: 69.09% C; 6.85% H; 7.33% N. Found: 68.67% C; 6.88% H; 7.28% N.

EXAMPLE 54

7-Bromo-1,2,3,3a,8,8a-hexahydro-5-methoxy-3a,8-dimethyl-1-(2-propenyl)-pyrrolo[2,3-b]indole A solution prepared from d,1-7-bromonoresermethole (4.00 g), diisopropylethylamine (5.22 g) and 25 ml of dry acetonitrile was degassed and stirred at 0° C. under nitrogen as a solution of allyl bromide (1.79 g) in 35 ml of dry acetonitrile was added dropwise. The solution was stirred at ambient temperature for four hours and then the solvent was evaporated. The residue was basified with $NaHCO_3$ solution and extracted with dichloromethane. The combined organic extracts were dried ($Na_2SO_4$), filtered and concentrated. One (1) gram of crude, previously prepared material, was combined with the residue and the combined material was purified by flash chromatography (silica; 4:1 hexane/EtOAc) and distilled under vacuum in a Kugelrohr (oven temperature=140° C./0.3 mm Hg) to give 4.2 g of the pure product as an oil.

ANALYSIS: Calculated for $C_{16}H_{21}BrN_2O$: 56.98% C; 6.28% H; 8.31% N. Found: 56.98% C; 6.28% H; 8.33% N.

EXAMPLE 55

1,2,3,3a,8,8a-Hexahydro-5-methoxy-3a,8-dimethyl-1-(3-methyl-2-butenyl)-pyrrolo[2,3-b]indole hydrochloride A solution prepared from d,1-noresermethole (8.10 g), diisopropylethylamine (14.39 g) and 25 ml of dry acetonitrile was degassed and stirred at 0° C. under nitrogen as a solution of 4-bromo-2-methyl-2-butene (6.08 g) in 40 ml of dry acetonitrile was added dropwise. The solution was stirred at ambient temperature for two hours and then the solvent was evaporated. The residue was purified by HPLC (silica; 3% MeOH/DCM) and then distilled under vacuum in a Kugelrohr (oven temperature=135° C./0.6 mm Hg) to give 4.8 g of oil. This material was dissolved in cold ether and treated with ethereal HCl until acidic to wet Litmus paper. The precipitate was collected and recrystallized from dichloromethane/ether to give 2.6 g of white crystals, mp 132°–133° C.

ANALYSIS: Calculated for $C_{18}H_{26}N_2O.HCl$: 66.96% C; 8.43% H; 8.68% N. Found: 66.67% C; 8.20% H; 8.70% N.

EXAMPLE 56

7-Bromo-1,2,3,3a,8,8a-hexahydro-5-methoxy-3a,8-dimethyl-1-(3-methyl-2-butenyl)-pyrrolo[2,3-b]indole A solution prepared from d,1-7-bromonoresermethole (5.00 g), diisopropylethylamine (6.52 g) and 30 ml of acetonitrile was degassed and stirred at 0° C. under nitrogen as a solution of 4-bromo-2-methyl-2-butene (2.76 g) in 35 ml of acetonitrile was added dropwise. The solution was stirred at 0° C. under nitrogen for three hours and then the acetonitrile was evaporated. The residue was purified by flash chromatography (silica; 3:1 hexane/EtOAc) and distilled under vacuum in a Kugelrohr (oven temperature=145° C./0.3 mm Hg) to give 3.7 g of the pure product as an oil.

ANALYSIS: Calculated for $C_{18}H_{25}BrN_2O$: 59.18% C; 6.90% H; 7.67% N. Found: 59.33% C; 7.00% H; 7.71% N.

EXAMPLE 57

7-Bromo-1,2,3,3a,8,8a-hexahydro-3a,8-dimethyl-1-(3-methyl-2-butenyl)-pyrrolo[2,3-b]indol-5-ol salicylate A solution of boron tribromide (40 ml of 1.0M in dichloromethane) was stirred at −10° C. under nitrogen as a solution of 7-bromo-1,2,3,3a,8,8a-hexahydro-5-methoxy-3a,8-dimethyl-1-(3-methyl-2-butenyl)-pyrrolo[2,3-b] indole (4.15 g) in 50 ml of dry DCM was added dropwise. The slurry was stirred at ambient temperature for three hours and then quenched with 100 ml of NaHCO$_3$ solution added dropwise. An additional 400 ml of NaHCO$_3$ solution was added and the mixture stirred under a stream of nitrogen for 20 minutes. The mixture was extracted with 4:1 chloroform/isopropanol, dried (Na$_2$SO$_4$), filtered and concentrated to give an oil. This material was purified twice by flash chromatography (silica; 3–5% MeOH/DCM) and converted to the salicylate salt in ether with 2 ml of ethanol added for solubility. More ether was added and the solution cooled to give 0.73 g of off-white crystals, mp 185°–187° C. (dec).

ANALYSIS: Calculated for $C_{17}H_{23}BrN_2O.C_7H_6O_3$: 58.90% C; 5.97% H; 5.73% N. Found: 58.73% C; 5.99% H; 5.70% N.

EXAMPLE 58

1-Cyclopropylmethyl-1,2,3,3a,8,8a-hexahydro-5-methoxy-3a,8-dimethylpyrrolo[2,3-b]indole hydrochloride A solution prepared from d,1-noresermethole (5.39 g), Hünig's base (15.96 g), bromomethyl-cyclopropane (5.00 g) and 25 ml of dry acetonitrile was degassed and stirred at reflux under nitrogen for one and a half hours. An additional 5.00 g of bromomethyl-cyclopropane in 25 ml of dry acetonitrile was added to the solution and reflux was continued another one and a half hours. The solvent was evaporated and the residue purified by flash chromatography (silica gel; toluene/EtOAc) to give 6.2 g of oil. This material was distilled under vacuum in a Kugelrohr (oven temperature=150°–170° C./0.4 mm Hg), dissolved in ether and treated with ethereal HCl until acidic to wet Litmus paper. The precipitate was collected and recrystallized from ethanol/ether to give white crystals, mp 184°–185° C.

ANALYSIS: Calculated for $C_{17}H_{24}N_2O.HCl$: 66.11% C; 8.16% H; 9.07% N. Found: 65.98% C; 8.10% H; 8.97% N.

EXAMPLE 59

1-Cyclopropylmethyl-1,2,3,3a,8,8a-hexahydro-3a,8-dimethylpyrrolo[2,3-b]indol-5-ol salicylate A 1.0M BBr$_3$ solution (70 ml) in dichloromethane (DCM) was diluted with 50 ml of dry DCM and stirred at −5° C. under nitrogen as 1-cyclopropylmethyl-1,2,3,3a,8,8a-hexahydro-5-methoxy-3a,8-dimethylpyrrolo[2,3-b]indole (5.40 g) dissolved in 60 ml of dry DCM was added slowly with a syringe. The mixture was stirred at 0° C. for one hour and then quenched by dropwise addition of 30 ml of water. The mixture was basified with aqueous K$_2$CO$_3$ and extracted with 4×150 ml of 4:1 chloroform/isopropanol. The combined organic extracts were dried (Na$_2$SO$_4$), filtered and concentrated. The residue was purified by column chromatography (200 g florisil; 5–10% MeOH/DCM) to give 4.3 g of oil. The salicylate salt of this material was formed in methanol/ether and crystallized out with the addition of ether. The collected precipitate was recrystallized from ethyl acetate/ether to give 2.5 g of crystals, mp 154°–157° C.

ANALYSIS: Calculated $C_{16}H_{22}N_2O.C_7H_6O_3$: 69.67% C; 7.12% H; 7.07% N. Found: 68.97% C; 7.19% H; 6.89% N.

EXAMPLE 60

1-Cyclopropylmethyl-1,2,3,3a,8,8a-hexahydro-3a,8-dimethylpyrrolo[2,3-b]indol-5-ol methyl carbamate ester A solution containing 1-cyclopropylmethyl-1,2,3,3a,8,8a-hexahydro-3a,8-dimethylpyrrolo[2,3-b]indol-5-ol (1.45 g) in 100 ml of dry tetrahydrofuran was degassed and stirred at room temperature under nitrogen as methyl isocyanate (1.92 g) was added in 3 portions at two hour intervals. The solution was stirred at room temperature under nitrogen overnight and then the solvent was evaporated. The residue was purified by column chromatography (alumina; 0→5% MeOH-/EtOAc) and recrystallized from ethyl acetate/pentane to give 1.1 g of white crystals, mp 168°–169° C.

ANALYSIS: Calculated for $C_{18}H_{25}N_3O_2$: 68.54% C; 7.99% H; 13.32% N. Found: 68.49% C; 8.06% H; 13.15% N.

EXAMPLE 61

7-Bromo-1-cyclopropylmethyl-1,2,3,3a,8,8a-hexahydro-5-methoxy-3a,8-dimethylpyrrolo[2,3-b]indole A solution prepared from d,1-7-bromonoresermethole (5.00 g), diisopropylethylamine (6.52 g), bromomethylcyclopropane (5.00 g) and 50 ml of acetonitrile was degassed and stirred at reflux under nitrogen for three hours. The acetonitrile was evaporated and the residue purified by flash chromatography (silica; 3:1 hexane/EtOAc) and then distilled under vacuum in a Kugelrohr (oven temperature=145° C./0.5 mm Hg) to give 3.55 g of pure product as an oil.

ANALYSIS: Calculated for $C_{17}H_{23}BrN_2O$: 58.12% C; 6.60% H; 7.98% N. Found: 58.09% C; 6.52% H; 7.80% N.

EXAMPLE 62

7-Bromo-1-cyclopropylmethyl-1,2,3,3a,8,8a-hexahydro-3a,8-dimethylpyrrolo[2,3-b]indol-5-ol salicylate A solution of boron tribromide (36 ml of 1.0M in dichloromethane) was stirred at −10° C. under nitrogen as a solution of 7-bromo-1-cyclopropylmethyl1,2,3,3a,8,8a-hexahydro-5-methoxy-3a,8-dimethylpyrrolo[2,3-b]indole (3.55 g) in 50 ml of dry dichloromethane was added dropwise. The resultant slurry was stirred at ambient temperature under nitrogen for three hours. The reaction was quenched with 100 ml of NaHCO₃ solution added dropwise. An additional 300 ml of NaHCO₃ solution was added and the slurry stirred for 20 minutes under a stream of nitrogen. The pH was adjusted to 8 with $K_2CO_3$ and then the product was extracted with 4:1 chloroform/isopropanol. The combined organic extracts were dried ($Na_2SO_4$), filtered and concentrated. The residue was purified by column chromatography (alumina; 3–7% MeOH/DCM) and then the salicylate salt was formed in ether with a little methanol added for solubility. Excess ether was added to induce crystallization and then recrystallization was conducted from ethyl acetate to obtain 2.7 g of white crystals, mp 180°–182° C.

ANALYSIS: Calculated for $C_{16}H_{21}BrN_2O\cdot C_7H_6O_3$: 58.11% C; 5.73% H; 5.89% N. Found: 57.89% C; 5.72% H; 5.75% N.

EXAMPLE 63

1,2,3,3a,8,8a-Hexahydro-5-methoxy-3a,8-dimethyl-1-(2-phenylethyl)-pyrrolo[2,3-b]indole hydrochloride A solution prepared from d,1-noresermethole (4.45 g), Hünig's base (13.17 g), (2-bromoethyl)benzene (7.55 g) and 100 ml of dry acetonitrile was stirred at reflux under nitrogen for one hour. More (2-bromoethyl)benzene (5.66 g) in 20 ml of acetonitrile was added and the solution stirred at reflux under nitrogen for an additional three hours. The solvent was evaporated and the residue combined with 1.9 g of previously prepared material. The combined material was purified by flash chromatography (silica gel; 1–2% MeOH/DCM) to give 7.6 g of oil. This oil was again purified by flash chromatography (silica gel; 6:1 toluene/EtOAc) to yield 6.8 g of nearly colorless oil. 3.0 g of this material was dissolved in 75 ml of ether and stirred at −10° C. as ethereal HCl was added dropwise. The resulting precipitate was collected and recrystallized from ethanol/ether to give 2.0 g of white crystals, mp 141°–142° C.

ANALYSIS: Calculated for $C_{21}H_{26}N_2O\cdot HCl$: 70.27% C; 7.58% H; 7.81% N. Found: 70.28% C; 7.53% H; 7.46% N.

EXAMPLE 64

1,2,3,3a,8,8a-Hexahydro-3a,8-dimethyl-1-(2phenylethyl)-pyrrolo[2,3-b]indol-5-ol salicylate A 1.0M BBr₃ solution (90 ml) in dichloromethane, (DCM) was stirred at −5° C. under nitrogen as 1,2,3,3a,8,8a-hexahydro-5-methoxy-3a,8-dimethyl-1-(2-phenylethyl)-pyrrolo[2,3-b]indole (8.30 g) dissolved in 100 ml of dry DCM was added dropwise. The mixture was stirred at 0° C. for one hour and then quenched by the dropwise addition of 50 ml of water. The mixture was diluted with 300 ml of saturated NaHCO₃ solution and stirred 20 minutes. The suspension was adjusted to pH 9 with $K_2CO_3$ and extracted with 4:1 chloroform/isopropanol. The combined organic extracts were dried ($Na_2SO_4$), filtered and concentrated. The salicylate of this material was formed in methanol/ether and crystallized out with the addition of more ether. The collected precipitate was recrystallized from ethyl acetate and then from acetonitrile to give 6.0 g of crystals, mp 132°–134° C.

ANALYSIS: Calculated for $C_{20}H_{24}N_2O\cdot C_7H_6O_3$: 72.62% C; 6.77% H; 6.28% N. Found: 72.25% C; 6.87% H; 6.12% N.

EXAMPLE 65

1,2,3,3a,8,8a-Hexahydro-3a,8-dimethyl-1-(2-phenylethyl)-pyrrolo[2,3-b]indol-5-ol, methyl carbamate ester A slurry prepared from 1,2,3,3a,8,8a-hexahydro-3a,8-dimethyl-1-(2-phenylethyl)-pyrrolo[2,3-b]indol-5-ol (5.65 g), milled potassium carbonate (2.53 g) and 75 ml of dry tetrahydrofuran was degassed and stirred at room temperature as methyl isocyanate (1.05 g) was added. The slurry was stirred under nitrogen overnight. The potassium carbonate was filtered off and washed with tetrahydrofuran. The combined tetrahydrofuran solution was concentrated and the residue purified by column chromatography (alumina; 3–5% MeOH/DCM). This material was then triturated with hot ethyl acetate to give an off-white solid, which was then recrystallized from isopropanol/ether to give 1.6 g of white crystals, mp 174°–176° C.

ANALYSIS Calculated for $C_{22}H_{27}N_3O_2$: 72.30% C; 7.45% H; 11.50% N. Found: 72.12% C; 7.47% H; 11.38% N.

EXAMPLE 66

7-Bromo-1,2,3,3a,8,8a-hexahydro-5-methoxy-3a,8-dimethyl-1-(2-phenylethyl)-pyrrolo[2,3-b]indole hydrobromide A solution prepared from d,1-7-bromonoresermethole (9.00 g), diisopropylethylamine (13.70 g), phenethyl bromide (16.81 g), and 50 ml of acetonitrile was degassed and stirred at reflux under nitrogen for three hours. The acetonitrile was evaporated and the residue was diluted with 400 ml of water and extracted with EtOAc. The combined organic extracts were dried ($Na_2SO_4$), filtered and concentrated. This material was purified by HPLC (silica; 3:1 hexane/EtOAc) and distilled in a Kugelrohr (oven temperature=190° C./0.35 mm Mg) to give 7.8 g of oil. 5.0 of this material was dissolved in ether and treated with ethereal HBr until acidic to wet Litmus paper. The solid was collected and recrystallized from ethanol/ether to give 4.2 g of white crystals, mp 169°–171° C.

ANALYSIS: Calculated for $C_{21}H_{25}BrN_2O.HBr$: 52.30% C; 5.43% H; 5.81% N. Found: 52.27% C; 5.42% H; 5.73% N.

EXAMPLE 67

7-Bromo-1,2,3,3a,8,8a-hexahydro-3a,8-dimethyl-1-(2-phenylethyl)-pyrrolo[2,3-b]indol-5-ol salicylate A solution of boron tribromide (45 ml of 1.0M in dichloromethane) was stirred at −10° C. under nitrogen as a solution of 7-bromo-1,2,3,3a,8,8a-hexahydro-5-methoxy-3a,8-dimethyl-1-(2-phenylethyl)pyrrolo[2,3-b]indole (5.10 g) in 60 ml of dry DCM was added dropwise. The resultant slurry was stirred at ambient temperature for three hours and then quenched with 100 ml of $NaHCO_3$ solution added dropwise. The slurry was diluted with another 400 ml of $NaHCO_3$ solution and stirred for 20 minutes under a stream of nitrogen. The mixture was extracted with 4:1 chloroform/isopropanol, dried ($Na_2SO_4$), filtered, and concentrated. The residue was purified by column chromatography (alumina; 3-6% MeOH/DCM) and converted to the salicylate salt in ether with one to two ml of methanol added for solubility. More ether was added and the solution cooled to induce crystallization. The material was recrystallized from ethyl acetate to give 2.8 g of white crystals, mp 190°–192° C. (dec.).

ANALYSIS: Calculated for $C_{20}H_{23}BrN_2O.C_7H_6O_3$: 61.72% C; 5.56% H; 5.33% N. Found: 61.86% C; 5.68% H; 5.27% N.

EXAMPLE 68

(3aS-cis)-1,2,3,3a,8,8a-Hexahydro-1,3a,7,8-tetramethyl-pyrrolo[2,3-b]indol-5-ol

A solution of 7-methyl-5-triisopropylsilyl-eseroline (2.94 g, See Example 86) in tetrahydrofuran (THF, 10 ml) was treated with tetrabutylammonium fluoride (7.5 ml, 1M in THF) under nitrogen at room temperature for 20 minutes. To the solution was added 10 ml of water, and the solution was concentrated on a rotary evaporator to remove the tetrahydrofuran. The mixture was then partitioned between water (100 ml) and ether (70 ml). The aqueous phase was separated and extracted with ether (2×70 ml). The combined ether solution was washed with brine (100 ml), dried over $MgSO_4$ and concentrated to an oil (about 2.37 g). This oil was triturated with hexane (3×50 ml) to a solid (1.22 g). This solid was taken into ether (50 ml) and the resultant solution was filtered and concentrated down to 15 ml. Crystals formed gradually when the solution was cooled. The crystals were collected and dried to give 0.87 g, mp 146°–148° C.

ANALYSIS: Calculated for $C_{14}H_{20}N_2O$: 72.37% C; 8.68% H; 12.06% N. Found: 72.24% C; 8.40% H; 11.94% N.

EXAMPLE 69

(3aS-cis)-7-Bromo-1,2,3,3a,8,8a-hexahydro-5-methoxy-1,3a,8-trimethylpyrrolo[2,3-b]indole fumarate A mixture of 7-bromoeseroline (10.24 g), sodium bicarbonate (3.0 g) and tetrahydrofuran (150 ml) was degassed and kept under nitrogen in an ice bath. Potassium t-butoxide (4.21 g) was charged and the mixture was stirred for 40 minutes to deprotonate the phenol. Methyl iodide (9.76 g) was added via a syringe in one portion. A precipitate formed in about 15 minutes. After 1.5 hours, the mixture was filtered and the solids were rinsed with ethyl acetate (100 ml). The organic solution was concentrated to an oil (5.85 g), which was purified on a flash chromatography column. Fractions containing the desired product were pooled together and concentrated to an oil (1.61 g). The oil was triturated with ether, whereupon a solid (510 mg) precipitated out, and was removed by filtration. The filtered ether solution was treated with a solution of fumaric acid (0.53 g) in methanol (4 ml) to give 1.34 g of white crystals, mp 149°–150° C.

ANALYSIS: Calculated for $C_{14}H_{19}BrN_2O.C_4H_4O_4$: 50.59% C; 5.42% H; 6.56% N. Found: 50.60% C; 5.52% H; 6.62% N.

EXAMPLE 70

(3aS-cis)-1,2,3,3a,8,8a-Hexahydro-5-methoxy-1,3a,8-trimethyl-7-nitropyrrolo[2,3-b]indole fumarate A solution of N-nitropyridinium tetrafluoroborate (4.2 g) in anhydrous acetonitrile (40 ml) was added dropwise to a stirred solution of esermethole (2.19 g) in acetonitrile (40 ml, degassed) under nitrogen at −10° C. (MeOH/ice). The progress of the reaction was followed by color change and by TLC on silica gel plates until the spot of starting material disappeared. The mixture was stirred at ambient temperature for a half (½) hour and partitioned in a mixture of brine/ice/ethyl acetate (200 ml:100 ml:200 ml). The organic phase was separated. The aqueous phase was extracted with ethyl acetate (2×100 ml). The combined ethyl acetate solution was washed with brine (200 ml), dried over $MgSO_4$, filtered and concentrated to an oil. This oil was purified by flash chromatography. The purest fractions were combined and concentrated to an oil (796 mg). This material was wetted with chloroform (4 ml) and dissolved into ether (300 ml). The solution was filtered once and treated with a solution of fumaric acid (331 mg) in warm methanol (about 5 ml). The final solution was concentrated down slowly to 60 ml and allowed to stand in a freezer for four hours. The product crystallized to give 877 mg, mp 156°–157° C.

ANALYSIS: Calculated for $C_{14}H_{19}N_3O.C_4H_4O_4$: 54.95% C; 5.89% H; 10.68% N. Found: 54.82% C; 5.87% H; 10.67% N.

EXAMPLE 71

(3aS-cis)-1,2,3,3a,8,8a-Hexahydro-1,3a,7,8-tetramethyl-pyrrolo[2,3-b]indol-5-ol, methyl carbamate ester A mixture of 7-methyleseroline from Example 68 (190 mg), potassium carbonate (113 mg) and tetrahydrofuran (4 ml) was degassed and kept under nitrogen at room temperature. Methyl isocyanate (60 mg) was added and the mixture was stirred for 45 minutes. At the end of the reaction, the mixture was filtered and the solid rinsed with ether. The solvent was removed and the crude residue was purified twice by flash chromatography on a silica gel column eluted with 1% $CH_3OH/DCM$. Fractions containing the pure product were pooled and concentrated to an oil (118 mg). Crystallization from a mixture of ether and isopropyl ether (0.3:0.3 ml) gave white crystals (76 mg), mp 117°–118° C.

ANALYSIS: Calculated for $C_{16}H_{23}N_3O_2$: 66.41% C; 8.01% H; 14.52% N. Found: 65.81% C; 7.86% H; 14.38% N.

EXAMPLE 72

(3aS-cis)-1,2,3,3a,8,8a-Hexahydro-1,3a,6,8-tetramethyl-pyrrolo[2,3-b]indol-5-ol, N,N-diethyl carbamate ester A solution of diethyl carbamate ester of eseroline (3.9 g) in tetrahydrofuran (50 ml) was degassed and chilled to −78° C. under nitrogen. s-Butyllithium (13 ml, 1.3M in cyclohexane) was added in one portion. The mixture was stirred for a half (½) hour. Methyl iodide (3.0 g) was added dropwise and the reaction mixture was stirred for 30 minutes. At the end of the reaction, the solvent was removed with a rotary evaporator and the residue partitioned between ethyl acetate (EtOAc, 150 ml) and a sodium bicarbonate solution (50 ml). The EtOAc was separated and the aqueous solution was extracted twice with EtOAc (2×100 ml). The combined EtOAc was washed with brine (100 ml) and dried over MgSO4. The solvent was removed to give a light yellow oil. Purification by flash chromatography on silica gel using 0.5% $CH_3OH$ in DCM as eluent afforded pure product as an oil weighing 2.3 g. It crystallized from a small volume of petroleum ether (5 ml) in a freezer to provide 1.10 g, mp 38°–40° C.

ANALYSIS: Calculated for $C_{19}H_{29}N_3O_2$: 68.85% C; 8.82% H; 12.68% N. Found: 69.07% C; 8.74% H; 12.68% N.

EXAMPLE 73

(3aS-cis)-6-chloro-1,2,3,3a,8,8a-hexahydro-1,3a,8-trimethylpyrrolo[2,3-b]indol-5-ol, N,N-diethyl carbamate ester A solution of diethyl carbamate ester of eseroline (2.5 g) in tetrahydrofuran (THF, 50 ml) was degassed and chilled to −78° C. (dry ice/acetone). s-Butyllithium (8.0 ml; 1.3M in cyclohexane) was added in one portion. The mixture was stirred for a half hour at −78° C. A solution of hexachloroethane (2.3 g) in THF (10 ml) was added dropwise over 10 minutes at low temperature and the mixture was stirred for one and a half hours. At the end of the reaction, the mixture was diluted with ethyl acetate (EtOAc, 10 ml), quenched with water (1 ml), and concentrated to about 10 ml. This mixture was then partitioned between EtOAc (150 ml) and a NaHCO3 (50 ml) solution. The EtOAc phase was separated and the aqueous solution was extracted once with EtOAc (150 ml). The combined EtOAc solution was washed with brine (100 ml), dried over MgSO4 and concentrated to an oil. Purification was conducted by flash chromatography on a silica gel column. The oil (2.1 g) thus obtained was dissolved in either, filtered and concentrated. Recrystallization twice from petroleum ether (7 ml, 15 ml) yielded 1.28 g of crystals, mp 51°–52° C.

ANALYSIS: Calculated for $C_{18}H_{26}ClN_3O_2$: 61.44% C; 7.45% H; 11.94% N. Found: 61.34% C; 7.49% H; 11.87% N.

EXAMPLE 74

(3aS-cis)-6-bromo-1,2,3,3a,8,8a-hexahydro-1,3a,8-trimethylpyrrolo[2,3-b]indol-5-ol, N,N-diethyl carbamate ester A solution of diethyl carbamate ester of eseroline (3.17 g) in tetrahydrofuran (35 ml) was degassed and chilled to −78° C. (dry ice/acetone) under nitrogen. s-Butyllithium (15 ml, 1.3M in cyclohexane) was added in one portion. The mixture was stirred for a half (½) hour and to this was added dropwise 5.9 g of 1,2-dibromoethane. The reaction was complete within 20 minutes, as indicated on TLC plates. The reaction mixture was diluted with ether (400 ml) and washed successively with NaHCO3 (2×150 ml) and brine. The ether solution was dried over MgSO4 and concentrated to an oil (about 6 g). This oil was dissolved in petroleum ether (40 ml). The desired product precipitated rapidly from the solution, was filtered and dried in a vacuum oven overnight at room temperature to give 1.67 g, mp 77°–78° C.

ANALYSIS: Calculated for $C_{18}H_{26}BrN_3O_2$: 54.55% C; 6.61% H; 10.60% N. Found: 54.60% C; 6.63% H; 10.49% N.

EXAMPLE 75

(3aS-cis)-7-Bromo-1,2,3,3a,8,8a-hexahydro-1,3a,8-trimethylpyrrolo[2,3-b]indol-5-ol benzoate ester, salicylate A solution of 7-bromoeseroline (4.53 g) in tetrahydrofuran (THF, 70 ml) was degassed and kept under nitrogen, and to this were added sodium bicarbonate (5.12 g) and potassium t-butoxide (2.68 g) in one portion. The mixture was stirred for one and a half hours at room temperature. Benzoyl anhydride (6.0 g) was added and the mixture was stirred for five hours. At the end of the reaction, the mixture was diluted with dichloromethane (DCM, 120 ml). The insolubles were filtered off. The filtrate was concentrated on a rotary evaporator to give 5.5 g of a crude solid/oil mixture. Purification was effected by flash chromatography twice on a silica gel column. Fractions containing the pure material were combined to afford 2.28 g of oil. The oil was dissolved in isopropyl ether (50 ml) and mixed with a solution of salicylic acid (787 mg) in isopropyl ether (50 ml). The volume was reduced to about 70 ml, during which crystallization occurred. The mixture was chilled in an ice bath for three hours and the crystals were collected (2.28 g), mp 160°–161° C.

ANALYSIS: Calculated for $C_{20}H_{21}BrN_2O_2 \cdot C_7H_6O_3$: 60.11% C; 5.05% H; 5.19% N. Found: 59.84% C; 5.02% H; 5.09% N.

EXAMPLE 76

(3aS-cis)-7-Bromo-1,2,3,3a,8,8a-hexahydro-1,3a,8-trimethylpyrrolo[2,3-b]indol-5-ol, 3,5-bis(1,1-dimethylethyl)-4-hydroxybenzoate A solution prepared from 3,5-di-tert-butyl-4-hydroxybenzoic acid (2.65 g), 1,1-carbonyldiimidazole (1.72 g) and 50 ml of dry tetrahydrofuran (THF) was stirred at reflux under nitrogen for 20 minutes and allowed to cool to 30° C. 7-Bromoeseroline (3.00 g) was added and the sides of the flask rinsed down with an additional 20 ml of dry THF. The solution was degassed and stirred under nitrogen at reflux for forty-eight hours. The solvent was evaporated and the residue purified by column chromatography (alumina; DCM). The resulting oil was crystallized from ether/pentane and then recrystallized from the same solvent system to give 1.17 g of white crystals, mp 133°–134° C.

ANALYSIS: Calculated for $C_{28}H_{37}BrN_2O_3$: 63.51% C; 7.04% H; 5.29% N. Found: 63.11% C; 7.10% H; 5.05% N.

EXAMPLE 77

(3aS-cis)-1,2,3,3a,8,8a-Hexahydro-1,3a,8-trimethylpyrrolo[2,3-b]indol-5-ol, cyclooctyl carbamate ester A degassed solution of eseroline (3 g) in 100 ml of dichloromethane was treated in one portion with 1,1'-carbonyldiimidazole (2.5 g) and stirred at room temperature for one hour. Cyclooctylamine (2.6 g) was added and the mixture was stirred overnight under nitrogen. The solution was concentrated to an oil and purified by HPLC (2% MeOH/DCM) to yield 0.95 g of oil, pure by TLC. The product crystallized from an ether/pentane mixture to yield 0.75 g of an off-white solid, mp 95°–96° C.

ANALYSIS: Calculated for $C_{22}H_{33}N_3O_2$: 71.11% C; 8.97% H; 11.31% N. Found: 71.15% C; 9.03% H; 11.38% N.

EXAMPLE 78

(3aS-cis)-1,2,3,3a8,8a-Hexahydro-1,3a,8-trimethylpyrrolo[2,3-b]indol-5-ol, N,N-(cyclooctyl)-methyl carbamate ester A degassed solution of eseroline (3 g) in 100 ml of dichloromethane was treated in one portion with 1,1'-carbonyldiimidazole (2.5 g) and stirred at room temperature for one hour under nitrogen. N-methylcyclooctylamine (3.9 g) was added and the mixture was stirred at room temperature overnight. The solution was concentrated to an oil and purified by HPLC (2% MeOH/DCM) to yield 1.6 g of oil which solidified upon standing for one hour. The solid was recrystallized from warm pentane to yield 1.1 g of the pure product, mp 109°–110° C.

ANALYSIS: Calculated for $C_{23}H_{35}N_3O_2$: 71.63% C; 9.17% H; 10.90% N. Found: 71.81% C; 9.22% H; 10.89% N.

EXAMPLE 79

(3aS-cis)-1,2,3,3a,8,8a-Hexahydro-1,3a,8-trimethylpyrrolo[2,3-b]indol-5-ol, [(S*)-1-(4-bromophenyl)ethyl] carbamate ester A degassed solution of eseroline (2 g) in 75 ml of tetrahydrofuran was treated with S-(−)-p-bromo-α-phenethylisocyanate (2.8 g) and a catalytic chip of sodium metal, and the mixture was refluxed overnight. The solution was concentrated and the residue purified by HPLC (2% MeOH/DCM) to yield the product as an oil (2.2 g). This oil was dissolved in ether and pentane was added, and the solution was allowed to stand overnight in a refrigerator, whereupon a solid crystallized (1.75 g). This solid was dissolved in 250 ml of ether, and the solution was swirled with charcoal and filtered. Upon concentration of the filtrate, a white cottony solid (1.2 g) precipitated from the solution, mp 180°–181° C.

ANALYSIS: Calculated for $C_{22}H_{26}BrN_3O_2$: 59.45% C; 5.91% H; 9.46% N. Found: 59.50% C; 5.96% H; 9.37% N.

EXAMPLE 80

(3aS-cis)-1,2,3,3a,8,8a-Hexahydro-1,3a,8-trimethylpyrrolo[2,3-b]indol-5-ol, [(S*)-(1-phenyl)ethyl methyl] carbamate ester A degassed solution of eseroline (4.0 g) in 80 ml of dry dichloromethane (DCM) was treated in one portion with 1,1'-carbonyldiimidazole (3.3 g) and stirred at room temperature for one hour. This solution was then treated with (S)-(−)-(α-methylbenzyl)methylamine (7.4 g) and stirred under reflux for one hundred twenty hours. The solution was concentrated and passed through a short pad of alumina (1:1 EtOAc/DCM) and purified by HPLC to give 4.0 g of pale oil. This oil was taken up in 100 ml of 8:1 petroleum ether/ether and chilled to give 3.38 g of crystals, mp 94°–96° C.

ANALYSIS Calculated for $C_{23}H_{29}N_3O_2$: 72.79% C; 7.70% H; 11.07% N. Found: 72.76% C; 7.81% H; 11.17% N.

EXAMPLE 81

(3aS-cis)-1,2,3,3a,8,8a-Hexahydro-1,3a,8-trimethylpyrrolo[2,3-b]indol-5-ol, [(R*)-(1-phenyl)ethyl methyl] carbamate ester A degassed solution of eseroline (2.0 g) in 60 ml of dry tetrahydrofuran was treated with 1,1'-carbonyldiimidazole (2.1 g) and stirred at room temperature. After one hour, this solution was treated with (R)-(+)-(α-methylbenzyl)methylamine (1.75 g) and two hours later treated with the same amount of the amine. The solution was stirred at 60° C. for sixty hours and thereafter concentrated. The residue was purified by flash chromatography (silica gel) to give 1.2 g of pale oil. This oil crystallized form 10 ml of 8:1 petroleum ether/ether to give 1.0 g of white crystals, mp 94°–96° C.

ANALYSIS: Calculated for $C_{23}H_{29}N_3O_2$: 72.79% C; 7.70% H; 11.07% N. Found: 72.92% C; 7.76% H; 11.11% N.

EXAMPLE 82

(3aS-cis)-1,2,3,3a,8,8a-Hexahydro-1,3a,8-trimethylpyrrolo[2,3-b]indol-5-ol, (2-phenyl)propyl carbamate ester fumarate A degassed solution of eseroline (2.2 g) and (2-phenyl)propylisocyanate (3.1 g) in 60 ml of dry tetrahydrofuran was stirred at room temperature for one hour and then refluxed for four hours. The solution was concentrated and the residue purified by flash chromatography (silica gel) to give 1.1 g of pale oil. This oil was taken up in 30 ml of methanol and treated with fumaric acid (0.34 g), and the solution was concentrated to a white foam. This foam was crystallized from a 2:15 methanol/ether solution to give 1.2 g of white cubes, mp 162°–164° C.

ANALYSIS: Calculated for $C_{23}H_{29}N_3O_2 \cdot C_4H_4O_4$: 65.43% C; 6.71% H; 8.47% N. Found: 65.36% C; 6.70% H; 8.44% N.

EXAMPLE 83

(3aS-cis)-1,2,3,3a,8,8a-Hexahydro-1,3a,8-trimethylpyrrolo[2,3-b]indol-5-ol, (−)-cis-myrtanyl carbamate ester A degassed solution of eseroline (3 g) in 30 ml of dichloromethane was treated in one portion with 1,1'-carbonyldiimidazole (2.5 g) and stirred at room temperature for one hour. (−)-cis-Myrtanylamine (2.7 g) was added and the mixture was stirred at room temperature overnight under nitrogen. The solution was concentrated and the residue was purified by HPLC using 2% MeOH/DCM to yield 0.95 g of solid product. The solid was recrystallized from a mixture of ether/pentane to yield pure crystalline product (0.45 g), mp 138°–139° C.

ANALYSIS: Calculated for $C_{24}H_{34}N_3O_2$: 72.67% C; 8.66% H; 10.60% N. Found: 72.43% C; 8.79% H; 10.54% N.

EXAMPLE 84

(3aS-cis)-1,2,3,3a,8,8a-Hexahydro-5-(methoxymethoxy)-1,3a,8-trimethylpyrrolo[2,3-b]indole fumarate A degassed solution of eseroline (9.1 g) in tetrahydrofuran (100 ml) was treated with potassium t-butoxide (5.6 g) for 30 minutes under nitrogen at 0° C. Bromomethyl methyl ether (6.8 g) was added in portions over 20 minutes. After stirring for one hour, the mixture was poured into degassed ethyl acetate (700 ml), washed with brine (3×100 ml), and dried over anhydrous MgSO$_4$. The solution was filtered and concentrated to an oil (11.35 g). This crude oil was purified by flash chromatography. The product was obtained as an oil weighing 5.68 g. A 2.1 g sample was further purified by a second flash chromatography. The product (1.42 g) was dissolved in ether (200 ml) and treated with a solution of fumaric acid (0.62 g) in ethanol (12 ml). The resultant solution was concentrated to about 60 ml with stirring. The product crashed out as off-white crystals (1.38 g), mp 126°-128° C.

ANALYSIS: Calculated for $C_{15}H_{22}N_2O_2 \cdot C_4H_4O_4$: 60.30% C; 6.93% H; 7.40% N. Found: 59.92% C; 6.85% H; 7.29% N.

EXAMPLE 85

(3aS-cis)-7-Bromo-1,2,3,3a,8,8a-hexahydro-5-triisopropylsilyloxy-1,3a,8-trimethylpyrrolo[2,3-b]indole trifluoromethanesulfonate salt 7-Bromoeseroline fumarate (10 g) suspended in dichloromethane (100 ml) was degassed and kept under nitrogen. 2,6-Lutidine (10.4 g) and triethylamine (2.45 g) were added to make a solution. At 0° C., triisopropylsilyl trifluoromethanesulfonate (TIPS-triflate, 22 g) was added in portions until the reaction was complete as shown on TLC plates over a period of four hours. The reaction mixture was concentrated. The crude mixture was dissolved in ether (450 ml) and washed with a NaHCO$_3$/brine solution (1:1, 300 ml×2). The ethereal solution was dried over MgSO$_4$ and concentrated to a waxy solid (24 g). The solid was recrystallized from ether (50 ml) and from isopropyl ether (100 ml) to give white fine crystals as triflate salt (2.85 g), mp 168°-169° C. The mother liquor was purified further by flash chromatography to yield 7.1 g of product free base as a light oil.

ANALYSIS: Calculated for $C_{22}H_{37}BrN_2OSi \cdot CF_3SO_3H$: 45.76% C; 6.35% H; 4.64% N. Found: 45.86% C; 6.33% H; 4.58% N.

EXAMPLE 86

(3aS-cis)-1,2,3,3a,8,8a-Hexahydro-1,3a,7,8-tetramethyl-5-triisopropylsilyloxy-pyrrolo[2,3-b]indole 7-Bromo-5-triisopropylsilyleseroline (6.3 g) in tetrahydrofuran (50 ml) was degassed and kept under nitrogen at −78° C. n-Butyllithium (14.2 ml, 2.5M in cyclohexane) was added slowly. The solution was stirred for 40 minutes, and thereafter 3.5 g of methyl iodide was added. The mixture was stirred for one hour at ambient temperature, concentrated to about 10 ml and extracted with ethyl acetate (EtOAc, 150 ml). The EtOAc solution was washed successively with NaHCO$_3$ and brine, and thereafter dried over Na$_2$SO$_4$. The solution was concentrated on a rotary evaporator to an oil (10.2 g). This was purified three times by flash chromatography over silica gel to afford the product as a colorless oil.

ANALYSIS: Calculated for $C_{22}H_{40}N_2OSi$: 71.07% C; 10.37% H; 7.21% N. Found: 70.80% C; 10.13% H; 7.07% N.

EXAMPLE 87

(3aS-cis)-7-Formyl-1,2,3,3a,8,8a-hexahydro-5-triisopropylsilyloxy-1,3a,8-trimethylpyrrolo[2,3-b]indole 7-Bromo-5-triisopropylsilyleseroline (1.53 g) in ether (10 ml) was degassed and kept under nitrogen at −78° C. A solution of t-butyllithium (2.2 ml, 1.7M in pentane) was added slowly. The resultant solution was stirred for one half (½) hour, and thereafter 2 ml of dimethylformamide was added. The mixture was stirred for 1.5 hours at −78° and then brought up to about 0° C. At the end of the reaction, the mixture was poured into a mixture of water and dichloromethane (50 ml/80 ml). The organic solution was separated and washed with brine (80 ml), dried over anhydrous MgSO$_4$ and concentrated to a crude oil. Purification was effected by flash chromatography over a silica gel column. The oil (770 mg) thus obtained was crystallized from petroleum ether to afford a waxy solid weighing 138 mg, mp 42°–45° C.

ANALYSIS: Calculated for $C_{23}H_{38}N_2O_2Si$: 68.61% C; 9.51% H; 6.96% N. Found: 68.51% C; 9.57% H; 6.89% N.

EXAMPLE 88

(3aS-cis)-7-Formyl-1,2,3,3a,8,8a-hexahydro-1,3a,8-trimethylpyrrolo[2,3-b]indol-5-ol, salicylate salt hemiethanolate 7-Formyl-5-triisopropylsilyleseroline (4.6 g) in tetrahydrofuran (THF, 25 ml) was degassed and kept under nitrogen. A 1M solution of tetrabutylammonium fluoride in THF (11 ml) was added dropwise at room temperature. The reaction was complete in about 15 minutes. The mixture was concentrated on a rotary evaporator to an oil. The oil was taken up in dichloromethane (DCM), washed successively with water and brine, and dried over MgSO$_4$. The DCM solution was concentrated to an oil again (about 5 g). Purification was conducted by flash chromatography over a silica gel column. The free base thus obtained was an oil weighing 2.76 g. This oil was dissolved in acetone (100 ml) and treated with a solution of salicylic acid (1.41 g) in acetone (40 ml). The acetone was removed under reduced pressure to leave a foam. Crystallization from CHCl$_3$ (10 ml) and isopropyl ether gave 2.76 g of solid. Two more recrystallizations from ethyl acetate (large volume) and ethanol (15 ml) yielded analytically pure product as crystals (0.87 g), mp 174°-175° C.

ANALYSIS: Calculated for $C_{14}H_{18}N_2O_2 \cdot C_7H_6O_3 \cdot 0.5\ C_2H_5OH$: 64.89% C; 6.68% H; 6.88% N. Found: 65.10% C; 6.70% H; 7.02% N.

EXAMPLE 89

(3aS-cis)-7-Formyl-1,2,3,3a,8,8a-hexahydro-1,3a,8-trimethylpyrrolo[2,3-b]indol-5-ol methyl carbamate ester To a solution of 7-formyleseroline (1.21 g) in tetrahydrofuran (THF, 10 ml, degassed) were added methylisocyanate (430 mg) and sodium (a chip). The mixture was stirred at room temperature for one hour under nitrogen. An additional 290 mg of isocyanate was added and the reaction was continued for one hour. The solvent was removed on a rotary evaporator. The crude mixture was purified by flash chromatography twice.

The material thus obtained was recrystallized from THF/hexane to give 560 mg of crystals, mp 181°–183° C.

ANALYSIS: Calculated for $C_{16}H_{21}N_3O_3$: 63.35% C; 6.98% H; 13.85% N. Found: 63.29% C; 6.97% H; 13.67% N.

EXAMPLE 90

(3aS-cis)-6-Formyl-1,2,3,3a,8,8a-hexahydro-1,3a,8-trimethylpyrrolo[2,3-b]indol-5-ol, N,N-diethylcarbamate ester salicylate hemihydrate A solution prepared from the diethylcarbamate of eseroline (3.12 g), tetramethylenediamine (TMEDA, 1.26 g) in ether (80 ml) and tetrahydrofuran (30 ml) was degassed and chilled to −78° C. s-Butyllithium (17 ml, 1.3M in hexane) was added in two portions over one and a half (1.5) hours. The mixture was stirred for an additional 40 minutes, and then quenched with dimethylformamide (3 ml). The mixture was poured into NaHCO$_3$ solution (400 ml) and extracted with ether (2×250 ml). The ether solution was washed with water and brine, and then dried over anhydrous MgSO$_4$. The solvent was removed on a rotary evaporator to give a crude oil (3.86 g). Purification was effected by flash chromatography on a silica gel column to give a light oil (3.0 g). This pure oil was treated with salicylic acid (1.3 g in 130 ml of ether) to give a gummy syrup. The supernatent was decanted, and the syrup was pumped to dryness as a foam.

ANALYSIS: Calculated for $C_{19}H_{27}N_3O_2 \cdot C_7H_6O_3 \cdot 0.5\ H_2O$: 63.42% C; 6.96% H; 8.53% N. Found: 63.83% C; 6.85% H; 8.08% N.

EXAMPLE 91

(3aS-cis)-6-Formyl-1,2,3,3a,8,8a-hexahydro-1,3a,8-trimethylpyrrolo[2,3-b]indol-5-ol salicylate hemihydrate A solution prepared from 6-formyl-N,N-diethylcarbamate ester of eseroline (960 mg) in ethanol (20 ml) and 10% NaOH (10 ml) was degassed and heated at 45° C. for 30 minutes. The solution was poured into degassed sodium bicarbonate solution (15 ml) and extracted with ethyl acetate (3×150 ml). The ethyl acetate solution was washed with brine (150 ml), dried over MgSO$_4$, and concentrated to an oil. Purification was effected by flash chromatography over silica gel using 1% CH$_3$OH/DCM. The pure product thus obtained weighed 722 mg as an oil. The oil was dissolved in ether (15 ml) and treated with a solution of salicylic acid (405 mg) in ether (20 ml). The crystalline product weighed 1.04 g, mp 156°–157° C.

ANALYSIS: Calculated for $C_{14}H_{18}N_2O_2 \cdot C_7H_6O_3 \cdot 0.5H_2O$: 64.11% C; 6.40% H; 7.12% N. Found: 64.13% C; 6.29% H; 7.24% N.

EXAMPLE 92

(3aS-cis)-1,2,3,3a,8,8a-Hexahydro-5-triisopropylsilyloxy-7-methylaminocarbonyl-1,3a,8-trimethylpyrrolo[2,3-b]indole A solution of 7-bromo-5-triisopropylsilyleseroline (19 g) in ether (120 ml) was degassed and cooled to −78° C. A solution of t-butyllithium (34.5 ml, 1.7M in pentane) was added dropwise. The solution was stirred for one hour and then 3.6 g of methylisocyanate was added. The mixture was stirred for one and a half (1.5) hours at −78° C. At the end of the reaction, the mixture was poured into ethyl acetate (700 ml). The solution was washed with water (400 ml) and brine (2×350 ml), dried over anhydrous MgSO$_4$ and concentrated to an oil (7.8 g). The crude oil was purified by flash chromatography over a silica gel column to afford 8.7 g of a pure oil.

EXAMPLE 93

(3aS-cis)-1,2,3,3a,8,8a-Hexahydro-7-methylaminocarbonyl-1,3a,8-trimethylpyrrolo[2,3-b]indol-5-ol To a solution of 7-methylaminocarbonyl-5-triisopropylsilyl-eseroline (2.1 g) in dry tetrahydrofuran (THF, 10 ml, degassed) was added a solution of tetrabutylammonium fluoride in THF (5 ml, 1M) at room temperature under nitrogen. The reaction was complete within 25 minutes. At the end of the reaction, the solvent was removed on a rotary evaporator. The product was purified by flash chromatography over a silica gel column using 1.5% CH$_3$OH/DCM. The purest fractions were pooled and concentrated to a white solid (1.4 g). Recrystallization from ethanol/ether/petroleum ether (5:20:5) gave white crystals (870 mg), mp 202°–203.5° C.

ANALYSIS: Calculated for $C_{15}H_{21}N_3O_2$: 65.42% C; 7.69% H; 15.26% N. Found: 64.86% C; 7.68% H; 15.03% N.

EXAMPLE 94

(3aS-cis)-1,2,3,3a,8,8a-Hexahydro-1,3a,8-trimethylpyrrolo[2,3-b]indol-5-ol, cyclododecyl carbamate ester A degassed solution of eseroline (4.5 g) in 90 ml of dichloromethane was treated in one portion with 1,1'-carbonyldiimidazole (3.7 g) and stirred at room temperature for two hours under nitrogen. Cyclododecylamine (7.5 g) was then added and the solution was stirred at room temperature overnight. The reaction mixture was concentrated to an oil. The oil was purified by column chromatography over neutral alumina to give 4.0 g of pale oil which solidified upon standing. Recrystallization from hexane gave 1.3 g of white powdery solid, mp 115°–116° C.

ANALYSIS: Calculated for $C_{26}H_{41}N_3O_2$: 73.01% C; 9.68% H; 9.83% N. Found: 72.95% C; 9.97% H; 9.66% N.

EXAMPLE 95

(3aS-cis)-1,2,3,3a,8,8a-Hexahydro-1,3a,8-trimethylpyrrolo[2,3-b]indol-5-ol, (2,3-dihydro-1H-inden-1-yl) carbamate ester salicylate A degassed solution of eseroline (4 g) in 75 ml of dichloromethane was treated in one portion with 1,1'-carbonyldiimidazole (3.57 g) and stirred at room temperature for one hour. 1-Aminoindan (2.44 g) was added to the solution which was then stirred for an additional eighteen hours. The solution was concentrated and the residue purified by HPLC to give 1.5 g of oil. The salicylate salt (0.9 g) was precipitated from a dilute ether/pentane solution. This salt was combined with another sample (1.3 g). Recrystallization from isopropyl ether yielded 1.1 g of a powdery solid, mp 88°–90° C.

ANALYSIS: Calculated for $C_{23}H_{27}N_3O_2 \cdot C_7H_6O_3$: 68.87% C; 6.46% H; 8.15% N. Found: 69.46% C; 6.58% H; 7.88% N.

EXAMPLE 96

(3aS-cis)-1,2,3,3a,8,8a-Hexahydro-1,3a,8-trimethylpyrrolo[2,3-b]indol-5-ol, 1-(1,2,3,4-tetrahydro)naphthyl carbamate ester A degassed solution of eseroline (2.0 g) in 60 ml of dry tetrahydrofuran was treated with neat 1,2,3,4-tetrahydronaphthylene-1-isocyanate (2.6 g) and a catalytic chip of sodium metal, and thereafter the mixture was stirred at room temperature for five hours. The solution was concentrated and the residue purified by flash chromatography over alumina to give 2.0 g of pale oil. This oil was crystallized from 10 ml of ether to give 1.3 g of white crystals, mp 170°-172° C.

ANALYSIS: Calculated for $C_{24}H_{29}N_3O_2$: 73.62% C; 7.46% H; 10.73% N. Found: 73.22% C; 7.53% H; 10.48% N.

EXAMPLE 97

(3aS-cis)-1,2,3,3a,8,8a-Hexahydro-1,3a,8-trimethylpyrrolo[2,3-b]indol-5-ol, [(R*)-1-(1-naphthyl)ethyl]carbamate ester A degassed solution of eseroline (2.0 g) in 75 ml of dry tetrahydrofuran was treated with (R)-(−)-1-(1-naphthyl)ethyl isocyanate (2.7 g) and a catalytic chip of sodium metal, and thereafter the mixture was refluxed overnight. The solution was concentrated and the residue purified by HPLC using 2% $CH_3OH/DCM$ to give 2.7 g of pale oil which crystallized from ethyl ether to give 2.0 g of white crystalline solid, mp 149°-150° C.

ANALYSIS: Calculated for $C_{26}H_{29}N_3O_2$: 75.15% C; 7.03% H; 10.11% N. Found: 74.98% C; 7.05% H; 9.99% N.

EXAMPLE 98

(3aS-cis)-1,2,3,3a,8,8a-Hexahydro-1,3a,8-trimethylpyrrolo[2,3-b]indol-5-ol, (1-adamantyl)methyl carbamate ester A degassed solution of eseroline (2.5 g) and (1-adamantyl)methyl isocyanate (3.0 g) in 60 ml of dry tetrahydrofuran was stirred at reflux for five hours. The resulting slurry was cooled to 0° C. and filtered. The filter cake was air dried and recrystallized twice from tetrahydrofuran to give 4.0 g of white crystals, mp 209°-211° C.

ANALYSIS: Calculated for $C_{25}H_{35}N_3O_2$: 73.31% C; 8.61% H; 10.26% N. Found: 73.47% C; 8.93% H; 10.28% N.

EXAMPLE 99

Hexahydro-(1H)-azepine carboxylic acid, (3aS-cis)-1,2,3,3a,8,8a-hexahydro-1,3a,8-trimethylpyrrolo[2,3-b]indol-5-yl ester fumarate A degassed solution of eseroline (2 g) in 40 ml of dichloromethane was treated in one portion with 1,1'-carbonyldiimidazole (1.8 g) and thereafter stirred at room temperature for one hour. Hexamethyleneimine (2.7 g) was added. After stirring overnight at room temperature under nitrogen, the solution was concentrated and the residue purified by HPLC using 2% $CH_3OH/DCM$ to give 1.5 g of oil. The fumarate salt was precipitated from methanol/ether to give 1.1 g of white crystals, mp 145°-147° C.

ANALYSIS: Calculated for $C_{20}H_{29}N_3O_2 \cdot C_4H_4O_4$: 62.72% C; 7.25% H; 9.14% N. Found: 62.75% C; 7.41% H; 9.14% N.

EXAMPLE 100

Octahydroazocine carboxylic acid, (3aS-cis)1,2,3,3a,8,8a-hexahydro-1,3a,8-trimethylpyrrolo[2,3-b]indol-5-yl ester fumarate A degassed solution of eseroline (2 g) in 50 ml of dichloromethane was treated in one portion with 1,1'-carbonyldiimidazole (1.8 g) and thereafter stirred at room temperature for one hour. Heptamethyleneimine (2.1 g) was added. After stirring overnight at room temperature under nitrogen, the solution was concentrated to a residue. Purification by HPLC using 3% $CH_3OH/DCM$ yielded a yellowish oil (1.4 g) which was fairly pure by TLC. The fumarate salt was precipitated from methanol/ether to yield 0.9 g. This product was combined with another sample (0.8 g prepared in a similar manner) and the total product was recrystallized from $CH_3OH$/ether to yield 1.3 g of pure salt, mp 135°-136° C.

ANALYSIS: Calculated for $C_{21}H_{31}N_3O_2 \cdot C_4H_4O_4$: 63.39% C; 7.46% H; 8.87% N. Found: 63.54% C; 7.41% H; 8.87% N.

EXAMPLE 101

(3aS-cis)-1,2,3,3a,8,8a-Hexahydro-1,3a,8-trimethylpyrrolo[2,3-b]indol-5-ol,(1,2,3,4-tetrahydroisoquinolinyl) carbamate ester A degassed solution of eseroline (3.0 g) in 80 ml of dry dichloromethane was treated in one portion with 1,1'-carbonyldiimidazole (2.7 g) and stirred at room temperature. After one hour, the solution was treated with 1,2,3,4-tetrahydroisoquinoline (4.0 g) and stirring was continued overnight. The solution was concentrated and the residue purified by flash chromatography to give 2.8 g of pale oil which was crystallized from ether to give 2.4 g of white crystals, mp 83°-85° C.

ANALYSIS: Calculated for $C_{23}H_{27}N_3O_2$: 73.18% C; 7.20% H; 11.13% N. Found: 72.98% C; 7.22% H; 11.09% N.

EXAMPLE 102

(3aS-cis)-1,2,3,3a,8,8a-Hexahydro-1,3a,8-trimethylpyrrolo[2,3-b]indol-5-ol, (1-methyl-1,2,3,4-tetrahydroisoquinolinyl) carbamate ester A degassed solution of eseroline (2.3 g) and 1,1'-carbonyldiimidazole (2.1 g) in 60 ml of dry dichloromethane was stirred at room temperature for one hour. This solution was treated with 1-methyl-1,2,3,4-tetrahydroisoquinoline (1.5 g) and stirred at 40° C. for two hours, and thereafter the same amount of said isoquinoline derivative was added and the solution was stirred at reflux for three hours. The solution was concentrated and the residue purified by column chromatography over alumina to give 2.0 g of pale oil. This oil was crystallized from 50 ml of a 10:1 pentane/ether solution to give 1.6 g of white crystals, mp 105°-108° C.

ANALYSIS: Calculated for $C_{24}H_{29}N_3O_2$: 73.62% C; 7.46% H; 10.73% N. Found: 73.86% C; 7.48% H; 10.65% N.

EXAMPLE 103

(3aS-cis)-1,2,3,3a,8,8a-Hexahydro-1,3a,8-trimethylpyrrolo[2,3-b]indol-5-ol, [3-[3-azabicyclo[3.2.2]nonyl]]carbamate ester fumarate A degassed solution of eseroline (2.5 g) in 30 ml of dichloromethane was treated in one portion with 1,1'-carbonyldiimidazole (2.1 g) and thereafter stirred at room temperature for one hour. 3-Azabicyclo[3.2.2]nonane (2.2 g) was added and this solution was stirred at room temperature under nitrogen for twelve hours. The reaction mixture was concentrated to a residue which was purified by chromatography over alumina to give 1.8 g of pale oil. This product was combined with another sample (1.4 g) prepared in a similar manner. The fumarate salt was crystallized from methanol/ether to yield 1.9 g of almost white crystals, mp 125°–126° C.

ANALYSIS: Calculated for $C_{22}H_{31}N_3O_2 \cdot C_4H_4O_4$: 64.30% C; 7.28% H; 8.65% N. Found: 63.81% C; 7.46% H; 8.47% N.

EXAMPLE 104

(3aS-cis)-1,2,3,3a,8,8a-Hexahydro-5-(methoxymethoxy)-1,3a,8-trimethyl-6-(trimethylsilyl)pyrrolo[2,3-b]indole hydrochloride A solution of 5-methoxymethyleseroline (9.25 g) in tetrahydrofuran (35 ml) was degassed and chilled to −78° C. s-Butyllithium (45 ml, 1.3M in cyclohexane) was added dropwise and the mixture was stirred for 45 minutes. Trimethylsilyl chloride (chlorotrimethylsilane; 11.3 g) was added dropwise at low temperature. The mixture was kept at −78° C. overnight (16 hours). At the end of the reaction period, the mixture was poured into ether (700 ml), washed successively with water (2×250 ml) and brine (2×250 ml) and dried with $MgSO_4$. The solution was concentrated to dryness to give an off-white solid (8.76 g). Recrystallization from ether (120 ml) gave a white crystalline solid (1.02 g), mp 188°–189° C.

ANALYSIS: Calculated for $C_{18}H_{30}N_2O_2Si \cdot HCl$: 58.27% C; 8.42% H; 7.55% N. Found: 58.31% C; 8.41% H; 7.46% N.

EXAMPLE 105

(3aS-cis)-1,2,3,3a,8,8a-Hexahydro-1,3a,8-trimethylpyrrolo[2,3-b]indol-5-ol, (1-adamantyl)carbamate ester A degassed solution containing eseroline (1.2 g) and freshly sublimed 1-adamantyl isocyanate (1.5 g) in 40 ml of dry tetrahydrofuran was stirred at reflux for thirty hours. This solution was concentrated and the residue purified by column chromatography to give 1.9 g of oil. This oil was crystallized from 15 ml of a 1:4 ether/pentane solution to give 1.3 g of white cubes, mp 105°–107° C.

ANALYSIS: Calculated for $C_{24}H_{33}N_3O_2$: 72.88% C; 8.41% H; 10.62% N. Found: 72.89% C; 8.47% H; 10.60% N.

We claim:

1. A compound of the formula

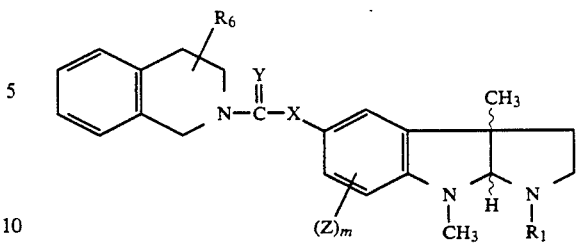

where
- (a) X is O or S;
- (b) Y is O or S;
- (c) m is 1 or 2;
- (d) each Z is independently H, loweralkyl, halogen, nitro, $-NH_2$, loweralkylcarbonylamino, arylcarbonylamino, loweralkoxycarbonylamino, loweralkylamino, triloweralkylsilyl, formyl, loweralkylaminocarbonyl, carboxyl or loweralkoxycarbonyl;
- (e) $R_1$ is H, loweralkyl, arylloweralkyl, heteroarylloweralkyl, cycloalkylmethyl or loweralkenylmethyl, and
- (f) $R_6$ is hydrogen or methyl; the term aryl in each occurrence signifying an unsubstituted phenyl group or naphthyl group or a phenyl group substituted with 1, 2 or 3 substituent groups each of which being independently loweralkyl, halogen, nitro, loweralkoxy, hydroxy or trifluoromethyl; and the term heteroaryl signifying a group having the formula

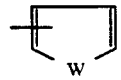

where W is O, S, $NR_5$ or $CH=N$, $R_5$ being hydrogen or loweralkyl; or a pharmaceutically acceptable acid addition salt thereof.

2. The compound as defined in claim 1, where the group $R_6$ is present at the 1-position of the tetrahydroisoquinoline ring.

3. The compound as defined in claim 1, where m is 1.

4. The compound as defined in claim 1, where X is O.

5. The compound as defined in claim 1, where m is 1 and X is O.

6. The compound as defined in claim 1, where Y is O.

7. The compound as defined in claim 1, where Z is H.

8. The compound as defined in claim 1, where Z is halogen.

9. The compound as defined in claim 1, where Z is 7-chloro or 7-bromo.

10. The compound as defined in claim 1, where Z is nitro, amino, loweralkylcarbonylamino, arylcarbonylamino, loweralkoxycarbonylamino or loweralkylamino.

11. The compound as defined in claim 1, where Y is S.

12. The compound as defined in claim 1, where Y is S and X is O.

13. The compound as defined in claim 1, where Y is O and X is S.

14. The compound as defined in claim 1, which is (3aS-cis)-1,2,3,3a,8,8a-hexahydro-1,3a,8-trimethylpyrrolo[2,3-b]indol-5-ol, (1,2,3,4-tetrahydroisoquinolinyl)

carbamate ester or the 3aR-cis isomer thereof or the racemic mixture or other mixture of the two.

15. The compound as defined in claim 1, which is (3aS-cis)-1,2,3,3a,8,8a-hexahydro-1,3,8-trimethylpyrrolo[2,3-b]indol-5-ol, (1-methyl-1,2,3,4-tetrahydroisoquinolinyl) carbamate ester or the 3aR-cis isomer thereof or the racemic mixture or other mixture of the two.

16. A pharmaceutical composition comprising an effective memory enhancing amount or pain alleviating amount of a compound as defined in claim 1 and a suitable carrier thereof.

17. A method of treating a patient in need of memory enhancement which comprises administering to the patient an effective amount of a compound as defined in claim 1.

18. A method of treating a patient in need of relief from pain which comprises administering to the patient an effective amount of a compound as defined in claim 1.

* * * * *